(12) United States Patent
Amin et al.

(10) Patent No.: US 6,313,137 B1
(45) Date of Patent: Nov. 6, 2001

(54) IMIDAZO PYRIDINE DERIVATIVES WHICH INHIBIT GASTRIC ACID SECRETION

(75) Inventors: Kosrat Amin; Mikael Dahlström, both of Mölndal; Peter Nordberg, Sävedalen; Ingemar Starke, Göteborg, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/319,973

(22) PCT Filed: Apr. 23, 1999

(86) PCT No.: PCT/SE99/00663

§ 371 Date: Jun. 14, 1999

§ 102(e) Date: Jun. 14, 1999

(87) PCT Pub. No.: WO99/55706

PCT Pub. Date: Nov. 4, 1999

(30) Foreign Application Priority Data

Apr. 29, 1998 (SE) .................................................. 9801526

(51) Int. Cl.[7] .......................... A61K 31/435; C07D 471/04
(52) U.S. Cl. ............................................. 514/300; 546/121
(58) Field of Search ............................... 546/121; 514/300

(56) References Cited

U.S. PATENT DOCUMENTS

| 4,450,164 | 5/1984 | Bristol et al. | ......................... 546/121 |
| 4,725,601 | 2/1988 | Ueda et al. | ............................ 514/300 |

FOREIGN PATENT DOCUMENTS

| 0033094 | 8/1981 | (EP) . |
| 0204285 | 12/1986 | (EP) . |
| 0228006 | 7/1987 | (EP) . |
| 0308917 | 3/1989 | (EP) . |

OTHER PUBLICATIONS

Kaminski, et al., J. Med. Chem. 28, 876–892 (1985).
Kaminski, et al., J. Med. Chem. 30, 2031–2046 (1987).
Kaminski, et al., J. Med. Chem. 30, 2047–2051 (1987).
Kaminski, et al., J. Med. Chem. 32, 1686–1700 (1989).
Kaminski, et al., J. Med. Chem. 34, 533–541 (1991).

*Primary Examiner*—Bernard Dentz
(74) *Attorney, Agent, or Firm*—White & Case LLP

(57) ABSTRACT

The present invention relates to imidazo pyridine derivatives of the formula (I), in which the phenyl moiety is substituted, and in which the imidazo pyridine moiety is substituted with a carboxamide group in 6-position, which inhibit exogenously or endogenously stimulated gastric acid secretion and thus can be used in the prevention and treatment of gastrointestinal inflammatory diseases.

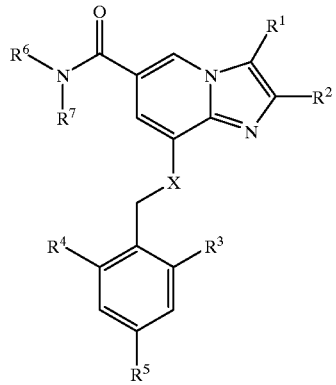

I

22 Claims, No Drawings

IMIDAZO PYRIDINE DERIVATIVES WHICH INHIBIT GASTRIC ACID SECRETION

This application is a 371 of PCT/SE99/00663 filed Apr. 23, 1999.

TECHNICAL FIELD

The present invention relates to novel compounds, and therapeutically acceptable salts thereof, which inhibit exogenously or endogenously stimulated gastric acid secretion and thus can be used in the prevention and treatment of gastrointestinal inflammatory diseases. In further aspects, the invention relates to compounds of the invention for use in therapy; to processes for preparation of such new compounds; to pharmaceutical compositions containing at least one compound of the invention, or a therapeutically acceptable salt thereof, as active ingredient; and to the use of the active compounds in the manufacture of medicaments for the medical use indicated above. The invention also relates to new intermediates for in the preparation of the novel compounds.

BACKGROUND ART

Substituted imidazo[1,2-a]pyridines, useful in the treatment of peptic ulcer diseases, are known in the art, e.g. from EP-B-0033094 and U.S. Pat. No. 4,450,164 (Schering Corporation); from EP-B-0204285 and U.S. Pat. No. 4,725,601 (Fujisawa Pharmaceutical Co.); and from publications by J. J. Kaminski et al. in the Journal of Medical Chemistry (vol. 28, 876–892, 1985; vol. 30, 2031–2046, 1987; vol. 30, 2047–2051, 1987; vol. 32, 1686–1700, 1989; and vol. 34, 533–541, 1991).

For a review of the pharmacology of the gastric acid pump (the H+, K+-ATPase), see Sachs et al. (1995) Annu. Rev. Pharmacol. Toxicol. 35: 277–305.

DISCLOSURE OF THE INVENTION

It has surprisingly been found that compounds of the Formula I, which are imidazo pyridine derivatives in which the phenyl moiety is substituted, and in which the imidazo pyridine moiety is substituted with a carboxamide group in 6-position are particularly effective as inhibitors of the gastrointestinal H+, K+-ATPase and thereby as inhibitors of gastric acid secretion.

In one aspect, the invention thus relates to compounds of the general Formula I

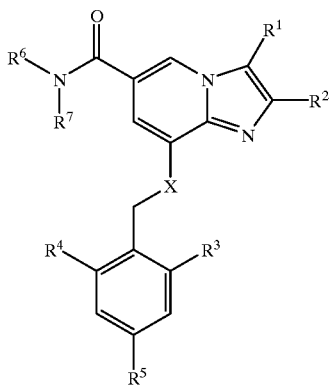

I or a pharmaceutically acceptable salt thereof, wherein $R^1$ is
(a) H,
(b) $CH_3$, or
(c) $CH_2OH$;

$R^2$ is
(a) $CH_3$
(b) $CH_2CH_3$ $R^3$ is
(a) H
(b) $C_1$–$C_6$ alkyl,
(c) hydroxylated $C_1$–$C_6$ alkyl
(d) halogen $R^4$ is
(a) H,
(b) $C_1$–$C_6$ alkyl,
(c) hydroxylated $C_1$–$C_6$ alkyl, or
(d) halogen;

$R^5$ is
(a) H, or
(b) halogen;

$R^6$, $R^7$ are the same or different
(a) H,
(b) $C_1$–$C_6$ alkyl;
(c) hydroxylated $C_1$–$C_6$ alkyl
(d) $C_1$–$C_6$ alkoxy-substituted $C_1$–$C_6$ alkyl X is
(a) NH, or
(b) O.

As used herein, the term "$C_1$–$C_6$ alkyl" denotes a straight or branched alkyl group having from 1 to 6 carbon atoms. Examples of said $C_1$–$C_6$ alkyl include methyl, ethyl, n-propyl, iso-propyl, n-butyl, iso-butyl, sec-butyl, t-butyl and straight- and branched-chain pentyl and hexyl.

The term "halogen" includes fluoro, chloro, bromo and iodo.

Both the pure enantiomers, racemic mixtures and unequal mixtures of two enantiomers are within the scope of the invention. It should be understood that all the diastereomeric forms possible (pure enantiomers, racemic mixtures and unequal mixtures of two enantiomers) are within the scope of the invention. Also included in the invention are derivatives of the compounds of the Formula I which have the biological function of the compounds of the Formula I, such as prodrugs.

It will also be appreciated by those skilled in the art, although derivatives of compounds of formula I may not possess pharmacological activity as such, they may be administered parenterally or orally and thereafter metabolised in the body to form compounds of the invention which are pharmacologically active. Such derivatives may therefore be described as "prodrugs". All prodrugs of compounds of formula I are included within the scope of the invention.

Depending on the process conditions the end products of the Formula I are obtained either in neutral or salt form. Both the free base and the salts of these end products are within the scope of the invention.

Acid addition salts of the new compounds may in a manner known per se be transformed into the free base using basic agents such as alkali or by ion exchange. The free base obtained may also form salts with organic or inorganic acids.

In the preparation of acid addition salts, preferably such acids are used which form suitably therapeutically acceptable salts. Examples of such acids are hydrohalogen acids such as hydrochloric acid, sulphuric acid, phosphoric acid, nitric acid, aliphatic, alicyclic, aromatic or heterocyclic carboxyl or sulphonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybensoic acid, embonic acid, methanesulphonic acid, ethanesulphonic acid, hydroxyethanesulphonic acid, halogenbensenesulphonic acid, toluenesulphonic acid or naphthalenesulphonic acid.

Preferred compounds according to the invention are those of the Formula I wherein $R^1$ is $CH_3$ or $CH_2OH$; $R^2$ is $CH_3$ or $CH_2CH_3$; $R^3$ is $CH_3$ or $CH_2CH_3$; $R^4$ is $CH_3$ or $CH_2CH_3$; $R^5$ is H, Br, Cl, or F.

Particularly preferred compounds according to the invention are:

2,3-dimethyl-8-(2-ethyl-6-methylbenzylamino)-N-propyl-imidazo[1,2-a]pyridine-6-carboxamide 8-(2-ethyl-6-methylbenzylamino)-3-hydroxymethyl-2-methylimidazo[1,2-a]pyridine-6-carboxamide 2,3-dimethyl-8-(2,6-dimethylbenzylamino)-N-hydroxyethyl-imidazo[1,2-a]pyridine-6-carboxamide 2,3-dimethyl-8-(2-ethyl-6-methylbenzylamino)-imidazo[1,2-a]pyridine-6-carboxamide 8-(2-ethyl-6-methylbenzylamino)-N,2,3-trimethylimidazo[1,2-a]pyridine-6-carboxamide 8-(2-ethyl-6-methylbenzylamino)-N,N,2,3-tetramethylimidazo[1,2-a]pyridine-6-carboxamide 2,3-dimethyl-8-(2,6-dimethylbenzylamino)-imidazo[1,2-a]pyridine-6-carboxamide 2,3-dimethyl-8-(2-ethyl-4-fluoro-6-methylbenzylamino)-imidazo[1,2-a]pyridine-6-carboxamide mesylate 2,3-dimethyl-8-(2-methylbenzylamino)-imidazo[1,2-a]pyridine-6-carboxamide 2,3-dimethyl-8-(2,6-dimethyl-4-fluoro-benzylamino)-imidazo[1,2-a]pyridine-6-carboxamide mesylate 2,3-dimethyl-8-(2-methyl-6-isopropylbenzylamino)-imidazo[1,2-a]pyridine-6-carboxamide mesylate 2,3-dimethyl-8-(2,6-dimethylbenzylamino)-imidazo[1,2-a]pyridine-6-carboxamide 2,3-dimethyl-8-(2-methylbenzylamino)-imidazo[1,2-a]pyridine-6-carboxamide 2,3 dimethyl-8-(2-ethyl-6-methylbenzylamino)-N-hydroxyethyl-imidazo[1,2-a]pyridine-6-carboxamide N-(2,3-dihydroxypropyl)-2,3 dimethyl-8-(2-ethyl-6-methylbenzylamino)-[1,2-a]pyridine-6-carboxamide 2,3 dimethyl-8-(2-ethyl-6-methylbenzylamino)-N-(2-methoxyethyl)-imidazo[1,2-a]pyridine-6-carboxamide 2-methyl-8-(2-ethyl-6-methylbenzylamino)-imidazo[1,2-a]pyridine-6-carboxamide 2,3-dimethyl-8-(2-bromo-6-methylbenzylamino)-imidazo[1,2-a]pyridine-6-carboxamide 2,3-dimethyl-8-(2-(2-hydroxyethyl)-6-methylbenzylamino)-imidazo[1,2-a]pyridine-6-carboxamide 8-(2-ethyl-6-methylbenzylamino)-N,N-bis(2-hydroxyethyl)-2,3-dimethylimidazo[1,2-a]pyridine-6-carboxamide 8-(2-ethyl-6-methylbenzylamino)-N-(2-hydroxyethyl)-N,2,3-trimethylimidazo[1,2-a]pyridine-6-carboxamide 2,3-dimethyl-8-(2-ethyl-6-methylbenzyloxy)-imidazo[1,2-a]pyridine-6-carboxamide Most preferred compounds according to the invention are:

8-(2-ethyl-6-methylbenzylamino)-3-hydroxymethyl-2-methylimidazo[1,2-a]pyridine-6-carboxamide 2,3-dimethyl-8-(2,6-dimethylbenzylamino)-N-hydroxyethyl-imidazo[1,2-a]pyridine-6-carboxamide 2,3-dimethyl-8-(2-ethyl-6-methylbenzylamino)-imidazo[1,2-a]pyridine-6-carboxamide 8-(2-ethyl-6-methylbenzylamino)-N,2,3-trimethylimidazo[1,2-a]pyridine-6-carboxamide 2,3-dimethyl-8-(2,6-dimethylbenzylamino)-imidazo[1,2-a]pyridine-6-carboxamide 2,3-dimethyl-8-(2-ethyl-4-fluoro-6-methylbenzylamino)-imidazo[1,2-a]pyridine-6-carboxamide 2,3-dimethyl-8-(2,6-dimethyl-4-fluoro-benzylamino)-imidazo[1,2-a]pyridine-6-carboxamide 2,3-dimethyl-8-(2,6-dimethylbenzylamino)-imidazo[1,2-a]pyridine-6-carboxamide 2,3 dimethyl-8-(2-ethyl-6-methylbenzylamino)-N-hydroxyethyl-imidazo[1,2-a]pyridine-6-carboxamide 2,3 dimethyl-8-(2-ethyl-6-methylbenzylamino)-N-(2-methoxyethyl)-imidazo[1,2-a]pyridine-6-carboxamide Preparation The present invention also provides the following processes A, B and C for the manufacture of compounds with the general Formula I.

Process A

Process A for manufacture of compounds with the general Formula I wherein X is NH comprises the following steps:

a) Compounds of the general Formula II

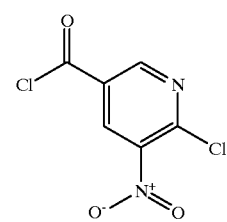

II can be reacted with amino compounds of the general Formula III

III wherein $R^6$ and $R^7$ are as defined for Formula I, to the corresponding amide of the Formula IV. The reaction can be carried out in standard conditions in an inert solvent.

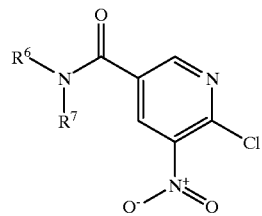

IV b) Compounds of the general Formula IV can be reacted with ammonia to compounds of the general Formula V

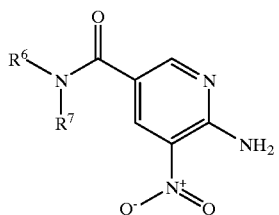

wherein $R^6$ and $R^7$ are as defined for Formula I. The reactions can be carried out under standard conditions in an inert solvent.

c) Compounds of the Formula V can be reduced e.g. by using hydrogen and a catalyst such as Pd/C to compounds of the Formula VI

VI

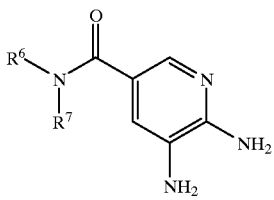

wherein $R^6$ and $R^7$ are as defined for Formula I. The reaction can be carried out under standard conditions in an inert solvent.

d) The imidazo[1,2-a]pyridine compounds of the Formula VIII can be prepared by reacting compounds of the general Formula VI with compounds of the general Formula VII

VII

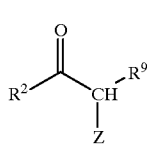

wherein $R^2$ is as defined for Formula I and Z is a leaving group such as halogen, mesyl, tosyl and $R^9$ represents H, $CH_3$ or an ester group such as $COOCH_3$, $COOC_2H_5$ etc.

The reaction is carried out under standard conditions in an inert solvent such as acetone, acetonitrile, alcohol, dimethylformamide, etc. with or without a base.

VIII

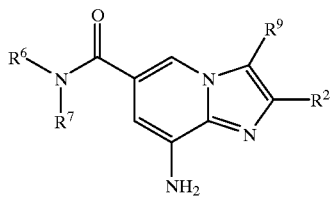

e) Compounds of the Formula VIII can be reacted with compounds of the Formula IX

IX

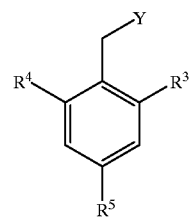

wherein $R^3$, $R^4$ and $R^5$ are as defined for Formula I and Y is a leaving group, such as a halide, tosyl or mesyl, to the compounds of the Formula X.

X

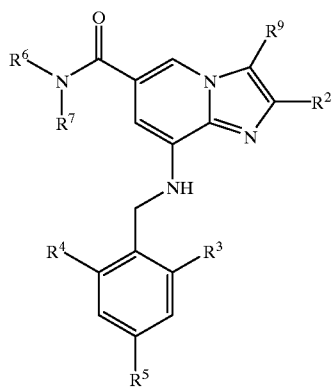

wherein $R^2$, $R^3$, $R^4$, $R^5$, $R^6$ and $R^7$ are as defined for Formula I and $R^9$ is H, $CH_3$ or an ester group such as $COOCH_3$, $COOC_2H_5$, etc. It is convenient to conduct this reaction in an inert solvent, e.g. acetone, acetonitrile, dimethoxyethane, methanol, ethanol or dimethylformamide with or without a base. The base is e.g. an alkali metal hydroxide, such as sodium hydroxide and potassium hydroxide, an alkali metal carbonate, such as potassium carbonate and sodium carbonate; or an organic amine, such as triethylamine.

f) Reduction of compounds of the general Formula X wherein $R^9$ is an ester group e.g. by using lithium borohydride in an inert solvent such as tetrahydrofuran or diethyl ether, to the compounds of the general Formula I wherein $R^1$ is $CH_2OH$.

Process B

Process B for manufacture of compounds with the general Formula I wherein $R^1$ is H or $CH_3$ and X is NH comprises the following steps:

a) Compounds of the general Formula II

II

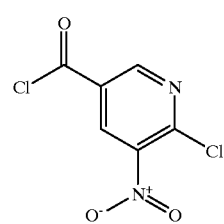

can be reacted with an alcohol compound of the general Formula $R^{10}$—OH, wherein $R^{10}$ is an alkyl group such as methyl, ethyl, etc. to the corresponding ester of Formula XI.

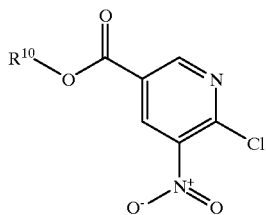

The reactions can be carried out under standard conditions.

b) Compounds of the general Formula XI can be reacted with ammonia to compounds of the general Formula XII

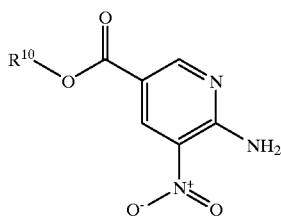

wherein $R^{10}$ is an alkyl group such as methyl or ethyl, etc. The reactions can be carried out under standard conditions in an inert solvent.

c) Compounds of the Formula XII can be reduced e.g. by using hydrogen and a catalyst such as Pd/C to compounds of the Formula XIII

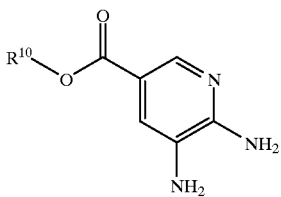

wherein $R^{10}$ is an alkyl group such as methyl, ethyl etc. The reaction can be carried out under standard conditions in an inert solvent.

d) The imidazo[1,2-a]pyridine compounds of the Formula XV wherein $R^{10}$ is an alkyl group such as methyl, ethyl etc, can be prepared by reacting compounds of the general Formula XIII with compounds of the general Formula XIV

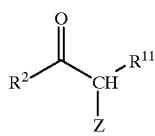

wherein $R^2$ is as defined for Formula I, Z is a leaving group such as halogen, mesyl or tosyl and $R^{11}$ represents H or $CH_3$. The reaction is carried out under standard conditions in an inert solvent such as acetone, acetonitrile, alcohol, dimethylformamide etc, with or without a base.

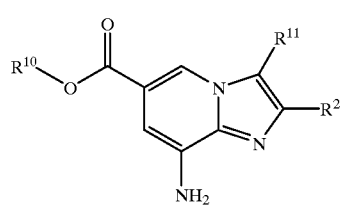

e) Compounds of the Formula XV can be reacted with compounds of the Formula IX

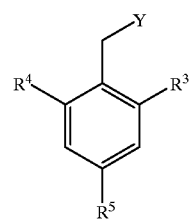

wherein $R^3$, $R^4$ and $R^5$ are as defined for Formula I and Y is a leaving group, such as a halide, tosyl or mesyl, to the compounds of the Formula XVI.

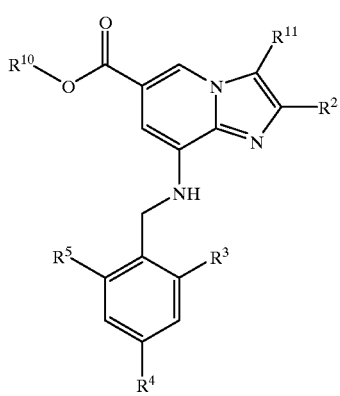

wherein $R^2$, $R^3$, $R^4$ and $R^5$ are as defined for Formula I, $R^{10}$ is an alkyl group such as methyl, ethyl, etc. and $R^{11}$ is H, or $CH_3$. It is convenient to conduct this reaction in an inert solvent, e.g. acetone, acetonitrile, dimethoxyethane, methanol, ethanol or dimethylformamide with or without a base. The base is e.g. an alkali metal hydroxide, such as sodium hydroxide and potassium hydroxide, an alkali metal carbonate, such as potassium carbonate and sodium carbonate; or an organic amine, such as triethylamine.

f) Compounds of the Formula XVI can be reacted with amino compounds of the general Formula III

III wherein $R^6$ and $R^7$ are as defined in Formula I to the corresponding amide of the Formula I wherein $R^1$ is H or $CH_3$ and X is NH. The reaction can be carried out by heating the reactants in the neat amino compound or in an inert solvent under standard conditions.

Process C

Process C for manufacture of compounds with the general Formula I comprises the following steps:

a) Treating compounds of Formula XVII

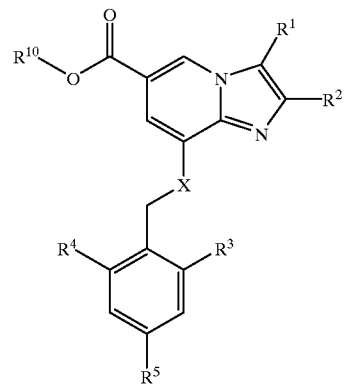

XVII wherein $R^1$, $R^2$, $R^3$, $R^4$, $R^5$, and X are as defined in Formula I and $R^{10}$ is an alkyl group such as methyl, ethyl, etc, with acid or base under standard conditions can hydrolyzed them to the corresponding carboxylic acid compounds of Formula XVIII

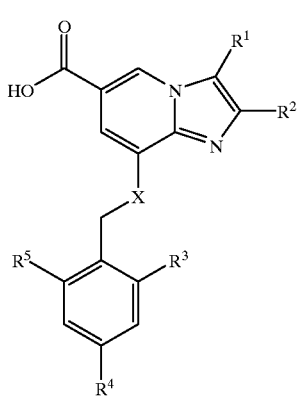

XVIII b) Compounds of the Formula XVIII wherein $R^1$, $R^2$, $R^3$, $R^4$, $R^5$ and X are as defined in Formula I can be reacted with amino compounds of Formula III in the presence of a coupling reagent to the corresponding amide compounds of the Formula I. The reaction can be carried out in an inert solvent under standard conditions.

Medical Use

In a further aspect, the invention relates to compounds of the formula I for use in therapy, in particular for use against gastrointestinal inflammatory diseases. The invention also provides the use of a compound of the formula I in the manufacture of a medicament for the inhibition of gastric acid secretion, or for the treatment of gastrointestinal inflammatory diseases.

The compounds according to the invention may thus be used for prevention and treatment of gastrointestinal inflammatory diseases, and gastric acid-related diseases in mammals including man, such as gastritis, gastric ulcer, duodenal ulcer, reflux esophagitis and Zollinger-Ellison syndrome. Furthermore, the compounds may be used for treatment of other gastrointestinal disorders where gastric antisecretory effect is desirable, e.g. in patients with gastrinomas, and in patients with acute upper gastrointestinal bleeding. They may also be used in patients in intensive care situations, and pre-and postoperatively to prevent acid aspiration and stress ulceration.

The typical daily dose of the active substance varies within a wide range and will depend on various factors such as for example the individual requirement of each patient, the route of administration and the disease. In general, oral and parenteral dosages will be in the range of 5 to 1000 mg per day of active substance.

Pharmaceutical Formulations

In yet a further aspect, the invention relates to pharmaceutical compositions containing at least one compound of the invention, or a therapeutically acceptable salt thereof, as active ingredient.

The compounds of the invention can also be used in formulations together with other active ingredients, e.g. antibiotics such as amoxicillin.

For clinical use, the compounds of the invention are formulated into pharmaceutical formulations for oral, rectal, parenteral or other mode of administration. The pharmaceutical formulation contains at least one compound of the invention in combination with one or more pharmaceutically acceptable ingredients. The carrier may be in the form of a solid, semi-solid or liquid diluent, or a capsule. These pharmaceutical preparations are a further object of the invention. Usually the amount of active compounds is between 0.1–95% by weight of the preparation, preferably between 0.1–20% by weight in preparations for parenteral use and preferably between 0.1 and 50% by weight in preparations for oral administration.

In the preparation of pharmaceutical formulations containing a compound of the present invention in the form of dosage units for oral administration the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatin capsules may be prepared with capsules containing a mixture of the active compound or compounds of the invention, vegetable oil, fat, or other suitable vehicle for soft gelatin capsules. Hard gelatin capsules may contain granules of the active compound. Hard gelatin capsules may also contain the active compound in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the active substance mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.1% to 20% by weight of the active ingredient and the remainder consisting of sugar or sugar alcohols and a mixture of ethanol, water, glycerol, propylene glycol and polyethylene glycol. If desired, such liquid preparations may contain coloring agents, flavoring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to by reconstituted with a suitable solvent extemporaneously before use.

The compounds according to the present invention can also be used in formulations, together or in combination for simultaneous, separate or sequential use, with other active ingredients, e.g. for the treatment or prophylaxis of conditions involving infection by *Helicobacter pylori* of human gastric mucosa. Such other active ingredients may be antimicrobial agents, in particular:

β-lactam antibiotics such as amoxicillin, ampicillin, cephalothin, cefaclor or cefixime;
macrolides such as erythromycin, or clarithromycin;
tetracyclines such as tetracycline or doxycycline;
aminoglycosides such as gentamycin, kanamycin or amikacin;
quinolones such as norfiloxacin, ciprofloxacin or enoxacin;
others such as metronidazole, nitrofurantoin or chloramphenicol; or
preparations containing bismuth salts such as bismuth subcitrate, bismuth subsalicylate, bismuth subcarbonate, bismuth subnitrate or bismuth subgallate.

The compounds according to the present invention can also be used together or in combination for simultaneous, separate or sequential use with antacids such as aluminium hydroxide, magnesium carbonate and magnesium hydroxid or alginic acid, or together or in combination for simultaneous, separate or sequential use with pharmaceuticals which inhibit acid secretion, such as, H2-blockers (e.g cimetidine, ranitidine), H+/K+-ATPase inhibitors (e.g. omeprazole, pantoprazole, lansoprazole or rabeprazole), or together or in combination for simultaneous, separate or sequential use with gastroprokinetics (e.g. cisapride or mosapride).

Intermediates

A further aspect of the invention is new intermediate compounds which are useful in the synthesis of compounds according to the invention.

Thus, the invention includes (a) a compound of the formula VIII

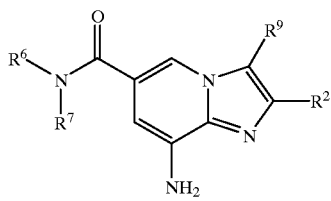

VIII wherein $R^2$, $R^6$ and $R^7$ are as defined for Formula I, and $R^9$ is H, $CH^3$ or an ester group such as $COOCH_3$, $COOC_2H_5$, etc.

(b) a compound of the formula X

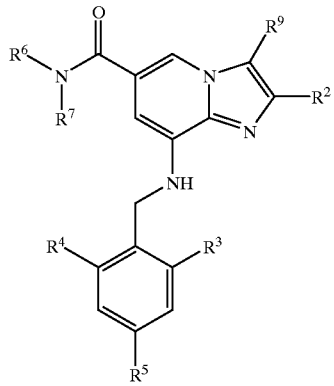

X wherein $R^2$, $R^3$, $R^4$, $R^5$, $R^6$ and $R^7$ are as defined for Formula I, and $R^9$ is an ester group such as $COOCH_3$, $COOC_2H_5$ etc.;

(c) a compound of the formula XV

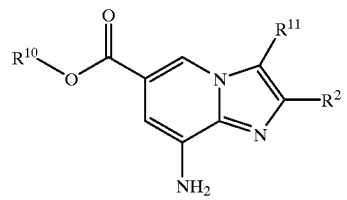

XV wherein $R^2$ is as defined for Formula I, $R^{10}$ is an alkyl group and $R^{11}$ is H or $CH_3$;

(d) a compound of the formula XVI

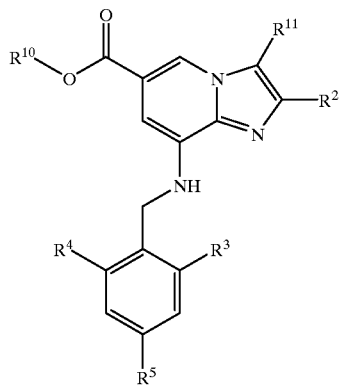

XVI wherein $R^2$, $R^3$, $R^4$ and $R^5$ are as defined for Formula I, $R^{10}$ is an alkyl group and $R^{11}$ is H or $CH^3$;

(e) a compound of the formula XVIII

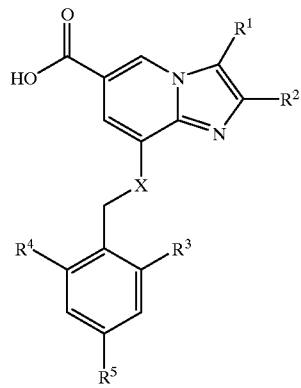

wherein $R^1$, $R^2$, $R^3$, $R^4$, $R^5$, and X are as defined for Formula I.

EXAMPLES

PREPARATION OF COMPOUNDS OF THE INVENTION

Example 1.1

Synthesis of 2,3-dimethyl-8-(2-ethyl-6-methylbenzylamino)-N-propyl-imidazo[1,2-a]pyridine-6-carboxamide

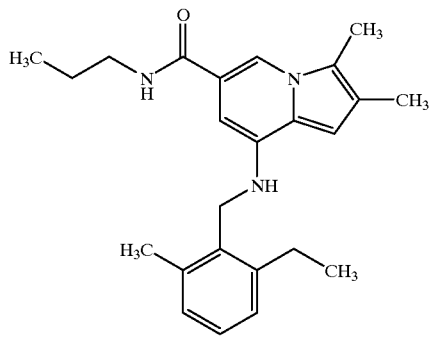

Ethyl 2,3-dimethyl-8-(2-ethyl-6-methylbenzylamino)-imidazo[1,2-a]pyridine-6-carboxylate (0.12 g, 0.33 mmol), propylamine (1.0 g, 17 mmol) and a cat. amount of sodium cyanide were refluxed in methanol (20 ml) for 24 h. An additional amount of propylamine (1.0 g, 17 mmol) was added and the reaction mixture was refluxed for 24 h. The solvent was evaporated under reduced pressure and the residue was purified by column chromatography on silica gel using dietyl ether as eluent. Crystallization from diethyl ether gave 0.053 g (42%) of the title compound.

$^1$H-NMR (300 MHz, CDCl$_3$): δ1.0 (t, 3H), 1.2 (t, 3H), 1.65–1.75 (m, 2H), 2.3 (s, 3H), 2.35 (s, 3H), 2.38 (s, 3H), 2.7 (q, 2H), 3.4–3.5 (m, 2H), 4.35 (d, 2H), 4.9 (bs, 1H) 6.35 (s, 1H), 7.0–7.2 (m, 4H), 7.85 (s, 1H).

Example 1.2

Synthesis of 8-(2-ethyl-6-methylbenzylamino)-3-hydroxymethyl-2-methylimidazo[1,2-a]pyridine-6-carboxamide

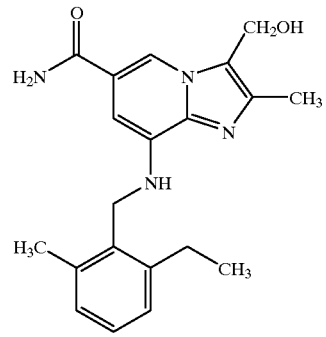

Ethyl 6-(aminocarbonyl)-8-(2-ethyl-6-methylbenzylamino)-2-methylimidazo[1,2-a]pyridine-3-carboxylate (280 mg, 0.71 mmol) and lithium borohydride (16 mg, 0.71 mmol) were added to tetrahydrofuran (10 ml) and the reaction mixture was refluxed for 70 min. Additional amounts of lithium borohydride (16 mg) and methanol (45 mg, 1.42 mmol) were added and the mixture was refluxed for 80 min. Additional amounts of lithium borohydride (16 mg) and methanol (22 mg, 71 mmol) were added and the mixture was refluxed for 4 h. The reaction mixture was allowed to reach R.T. and water (1 ml) and methanol (5 ml) and was stirred for 40 min. at R.T. The solvents were evaporated under reduced pressure and the residue was added to water and was stirred for 80 min. The crystals were filtered off and washed with water, ethyl acetate/ethanol and diethyl ether to give the desired product (115 mg, 46%).

$^1$H-NMR (300 MHz, DMSO-d$_6$): δ1.15 (t, 3H), 2.25 (s, 3H), 2.35 (s, 3H), 2.7 (q, 2H) 4.35 (d, 2H), 4.75 (d, 2H), 4.85 (t, 1H), 5.1 (t, 1H), 6.8 (s, 1H), 7.1–7.25 (m, 3H), 7.4 (bs 1H), 8.05 (bs, 1H), 8.3 (s, 1H)

Example 1.3

Synthesis of 2,3-dimethyl-8-(2,6-dimethylbenzylamino)-N-hydroxyethyl-imidazo[1,2-a]pyridine-6-carboxamide

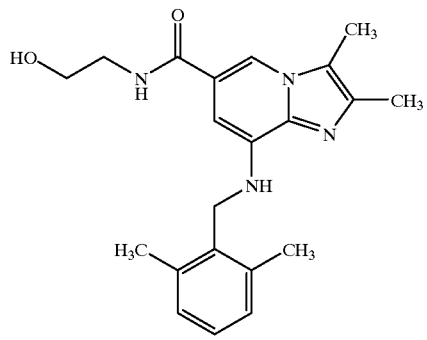

Methyl 2,3-dimethyl-8-(2,6-dimethylbenzylamino)-imidazo[1,2-a]pyridine-6-carboxylate (0.12 g, 0.33 mmol), ethanolamine (0.2 g, 3.3 mmol) and sodium cyanide (10 mg, 0.2 mmol) were refluxed in dimethoxyethane (2 ml) for 20 h. The solvent was evaporated under reduced pressure. Purification of the residue by column chromatography on silica gel using methylene chloride:methanol (92:8) as eluent gave the product which was washed with diethyl ether to give 103 mg (79%) of the title compound.

$^1$H-NMR (300 MHz, CDCl$_3$): δ2.3 (s, 6H), 2.35 (s, 6H), 3.5–3.6 (m, 2H), 3.75–3.8 (m, 2H), 4.3 (d, 2H), 4.95 (t, 1H), 6.4 (s, 1H), 6.85 (t 1H), 7.0–7.2 (m, 3H), 7.75 (s, 1H)

Example 1.4
Synthesis of 2,3-dimethyl-8-(2-ethyl-6-methylbenzylamino)-imidazo[1,2-a]pyridine-6-carboxamide

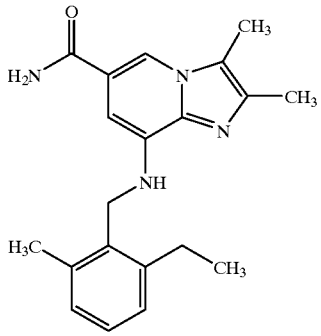

8-Amino-2,3-dimethylimidazo[1,2-a]pyridine-6-carboxamide (3.3 g, 16.2 mmol), 2-ethyl-6-methylbenzylchloride (2.73 g, 16.2 mmol), potassium carbonate (8.0 g, 58 mmol) and potassium iodide (1.1 g, 6.6 mmol) were added to acetone (150 ml) and refluxed for 20 h. An additional amount of 2-ethyl-6-methylbenzylchloride (1.0 g, 5.9 mmol) was added and the reaction mixture was refluxed for 7 h. Methylene chloride (60 ml) and methanol (30 ml) were added. The reaction mixture was filtered and the solvents were evaporated under reduced pressure. The residue was purified by column chromatography on silica gel using methylene chloride:methanol (100:7) as eluent. Crystallization from ethyl acetate gave 2.8 g (50%) of the title compound.

$^1$H-NMR (300 MHz, CDCl$_3$): δ1.2 (t, 3H), 2.34 (s, 3H), 2.36 (s, 3H), 2.38 (s, 3H), 2.7)(q, 2H), 4.4 (d, 2H), 4.9 (bs, 1H), 6.0 (bs, 2H), 6.45 (s, 1H), 7.0–7.2 (m, 3H), 7.9,(s, 1H).

Example 1.5
Synthesis of 8-(2-ethyl-6-methylbenzylamino)-N, 2,3-trimethylimidazo[1,2-a]pyridine-6-carboxamide

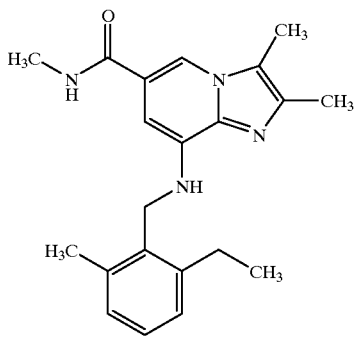

2,3-Dimethyl-8-(2-ethyl-6-methylbenzylamino)-imidazo[1,2-a]pyridine-6-carboxylic acid (0.15 g, 0.44 mmol) and o-Benzotriazol-1-yl-N,N,N',N'-Tetramethyluronium tetrafluoroborate (TBTU) (0.14 g, 0.44 mmol) were added to methylene chloride (10 ml) and the reaction mixture was stirred at room temperature for 15 min. Methylamine (0.1 g, 3.2 mmol) was added and the reaction mixture was stirred at ambient temperature for 1.5 h. The solvent was evaporated under reduced pressure and the residue was purified by column chromatography on silica gel using ethylacetate:methylene chloride (1:1) as eluent. The yield was treated with diethyl ether to give 40 mg (26%) of the desired product.

$^1$H-NMR (300 MHz, CDCl$_3$): δ1.2 (t, 3H), 2.33 (s, 3H), 2.36 (s, 3H), 2.38 (s, 3H), 2.7 (q, 2H), 3.05 (d, 3H), 4.35 (d, 2H), 4.9 (t, 1H), 6.3 (bs, 1H), 6.4 (s, 1H), 7.07–7.2 (m, 3H), 7.85 (s, 1H)

Example 1.6
Synthesis of 8-(2-ethyl-6-methylbenzylamino)-N,N,2,3-tetramethylimidazo[1,2-a]pyridine-6-carboxamide

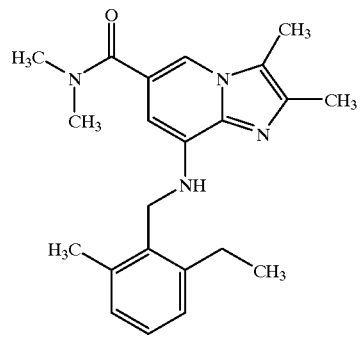

2,3-Dimethyl-8-(2-ethyl-6-methylbenzylamino)-imidazo[1,2-a]pyridine-6-carboxylic acid (0.15 g, 0.44 mmol) and o-Benzotriazol-1-yl-N,N,N',N'-Tetramethyluronium tetrafluoroborate (TBTU)(0.14 g, 0.44 mmol) were added to methylene chloride (10 ml). Dimethylamin (0.063 g, 1.4 mmol) was added and the reaction mixture was stirred at ambient temperature for 4 h. An additional amount of dimethylamin (0.1 ml) was added and the mixture was stirred at room temperature for 20 h. The solvent was evaporated under reduced pressure and the residue was purified by column chromatography using methylene chloride:methanol (9:1) as eluent. The oily product was treated with heptane and the solid that formed was filtered off to give 0.1 g (62%) of the title compound.

$^1$H-NMR (300 MHz, CDCl$_3$): δ1.2 (t, 3H), 2.35 (s, 6H), 2.4 (s, 3H), 2.7 (q, 2H), 3.15 (s, 6H), 4.4 (d, 2H), 4.9 (t, 1H), 6.25 (s, 1H), 7.0–7.2 (m, 3H), 7.45 (s, 1H)

Example 1.7
Synthesis of 2,3-dimethyl-8-(2,6-dimethylbenzylamino)-imidazo[1,2-a]pyridine-6-carboxamide

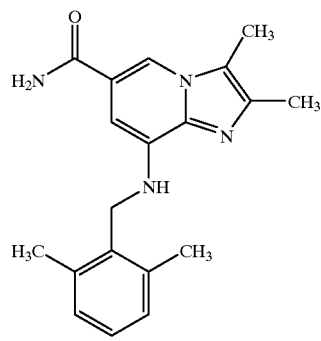

8-Amino-2,3-dimethylimidazo[1,2-a]pyridine-6-carboxamide (0.6 g, 2.9 mmol), 2,6-dimethylbenzylchloride (0.45 g, 2.9 mmol), sodium carbonate (1.0 g, 9.4 mmol) and potassium iodide (0.2 g, 1.3 mmol) were added to acetone (25 ml) and refluxed for 19 h. Methylene chloride was added and inorganic salts were filtered off. The solution was washed with a bicarbonate solution, the organic layer was separated, dried and the solvents were evaporated under reduced pressure. The residue was purified by column chromatography on silica gel using methylene chloride:methanol (100:5) as eluent and the product was washed with diethyl ether to give 0.78 g (82%) of the title compound.

$^1$H-NMR (500 MHz, CDCl$_3$): δ2.33 (s, 3H), 2.4 (s, 6H), 2.42 (s, 3H), 4.4 (d, 2H), 2.95 (bs, 1H), 6.45 (s, 1H), 7.05–7.15 (m, 3H), 7.95 (s, 1H)

Example 1.8

Synthesis of 2,3-dimethyl-8-(2-ethyl-4-fluoro-6-methylbenzylamino)-imidazo[1,2-a]pyridine-6-carboxamide mesylate

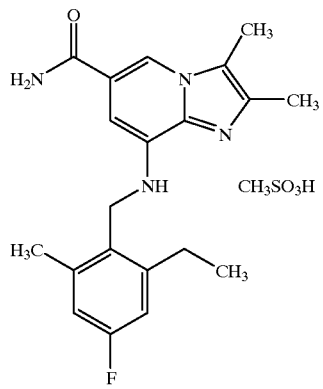

8-Amino-2,3-dimethylimidazo[1,2-a]pyridine-6-carboxamide mesylate (0.7 g, 1.9 mmol), 2-ethyl-4-fluoro-6-methylbenzylchloride (0.26 g, 1.9 mmol) and diisopropylethylamin (0.54 g, 4.2 mmol) were added to dimethylformamide (5 ml) and stirred at room temperature for 1 h. Methylene chloride and water were added to the reaction mixture, the organic layer was separated, dried and evaporated under reduced pressure. The residue was solved in ethylacetate and ethanol and metanesulfonic acid (0.2 g, 2 mmol) was added. The product was filtred off and was solved in methylene chloride:methanol (2:1) and an excess of potassium carbonate. The solids were filtred off and the solvent was evaporated under reduced pressure. The residue was purified by column chromatography on silica gel using methylene chloride:methanol (10:1) as eluent. The residue was solved in ethylacetate and methansulfonic acid (0.04 g, 0.4 mmol) was added. The salt was filtred off to give 0.2 g (23%) of the title compound.

$^1$H-NMR (300 MHz,DMSO-d$_6$): δ1.15 (t, 3H), 2.25 (s, 3H), 2.35 (s, 3H), 2.4 (s, 3H), 2.45 (s, 3H), 2.6 (q, 2H), 4.35 (d, 2H), 6.15 (bs, 1H), 6.95–7.05 (m, 2H), 7.4 (s, 1H), 7.8 (bs, 1H), 8.3 (bs, 1H), 8.45 (s, 1H)

Example 1.9

Synthesis of 2,3-dimethyl-8-(2-methylbenzylamino)-imidazo[1,2-a]pyridine-6-carboxamide

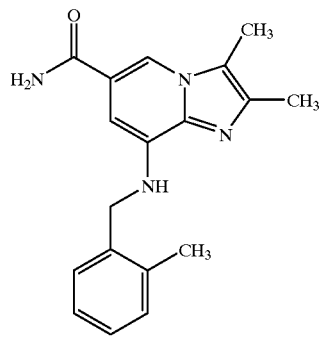

8-Amino-2,3-dimethylimidazo[1,2-a]pyridine-6-carboxamide mesylate (1.0 g, 2.7 mmol), α-chloro-o-xylene (0.38 g, 2.7 mmol) and diisopropylethylamin (0.76 g, 5.9 mmol) in dimethylformamide (7 ml) were stirred at 50° C. for 7 h and at room temperature for 72 h. The solvent was evaporated and the residue was treated with a mixture of methylene chloride, water and a small amount of diisopropylethylamin. The solid that formed was isolated by filtration and washed with ethylacetate to give 0.11 g (13%) of the title compound.

$^1$H-NMR (300 MHz,DMSO-d$_6$): δ2.3 (s, 3H), 2.35 (s, 3H), 2.4 (s, 3H), 4.45 (d, 2H), 6.3–6.4 (m, 2H), 7.1–7.25 (m, 4H), 7.3 (bs, 1H), 7.85 (bs, 1H), 8.05 (s, 1H)

Example 1.10

Synthesis of 2,3-dimethyl-8-(2,6-dimethyl-4-fluorobenzylamino)-imidazo[1,2-a]pyridine-6-carboxamide mesylate

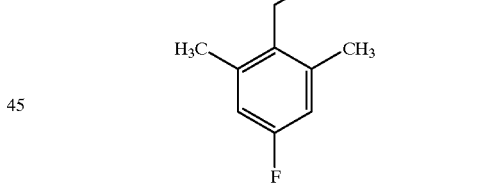

8-Amino-2,3-dimethylimidazo[1,2-a]pyridine-6-carboxamide mesylate (5.0 g, 13.4 mmol), 2,6-dimethyl-4-fluorobenzylbromide (2.91 g, 13.4 mmol), diisopropylethylamin (3.8 g, 29.5 mmol) and a cat. amount of potassium iodide were stirred in dimethylformamide (20 ml) at room temperature overnight. Water (70 ml) and methylene chloride (2×50 ml) were added to the reaction mixture and the organic layer was separated, dried and evaporated under reduced pressure. The residue was purified by column chromatography on silica gel using methylene chloride:methanol (9:1) as eluent. The product was solved in isopropanol and methansulfonic acid (0.3 g) was added. The salt that formed was isolated by filtration and washed with isopropanol and diethyl ether to give 1.4 g (24%) of the title compound.

$^1$H-NMR (500 MHz,DMSO-d$_6$): δ2.25 (s, 3H), 2.35 (s, 6H), 2.4 (s, 3H), 2.5 (s, 3H), 4.4 (d, 2H), 6.1 (bs, 1H), 7.0 (d, 2H), 7.35 (s, 1H), 7.8 (bs, 1H), 8.3 (bs, 1H), 8.45 (s, 1H)

Example 1.11

Synthesis of 2,3-dimethyl-8-(2-methyl-6-isopropylbenzylamino)-imidazo[1,2-a]pyridine-6-carboxamide mesylate

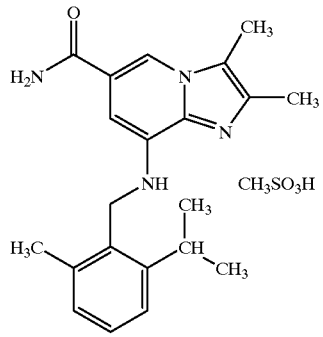

8-Amino-2,3-dimethylimidazo[1,2-a]pyridine-6-carboxamide mesylate (3.0 g, 8.0 mmol), 2-methyl-6-isopropylbenzylchloride (1.47 g, 8.0 mmol), diisopropylethylamin (2.4 g, 18.6 mmol) and a cat. amount of potassium iodide in dimethylformamide (15 ml).

The title compound were prepared according to Example 1.10 (Yield: 1.3 g, 36%)

$^1$H-NMR (300 MHz, DMSO-$d_6$): δ1.2 (d, 6H), 2.25 (s, 3H), 2.4 (s, 3H), 2.45 (s, 3H), 2.5 (s, 3H), 3.2 (m, 1H), 4.45 (d, 2H), 6.15 (bs, 1H), 7.15–7.3 (m, 3H), 7.4 (s, 1H), 7.85 (bs, 1H), 8.35 (bs, 1H), 8.45 (s, 1H)

Example 1.12

Synthesis of 2,3-dimethyl-8-(2,6-dimethylbenzylamino)-imidazo[1,2-a]pyridine-6-carboxamide

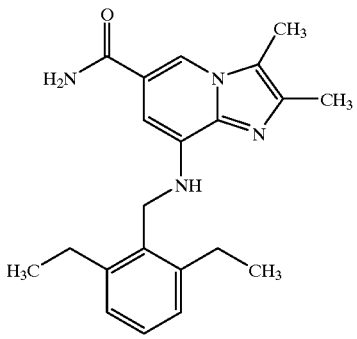

8-Amino-2,3-dimethylimidazo[1,2-a]pyridine-6-carboxamide mesylate (4.0 g, 10.7 mmol), 2,6-diethylbenzylchloride (1.8 g, 9.9 mmol), diisopropylethylamin (3.0 g, 23.3 mmol) were stirred in dimethylformamide (20 ml) at 50° C. overnight and at 70° C. for 3 h. Water (60 ml) and methylene chloride were added and the organic layer was separated, dried and evaporated under reduced pressure. The residue was treated with diethyl ether and the product was filtred off to give 1.7 g (45%) of the title compound.

$^1$H-NMR (300 MHz, CDCl$_3$): δ1.2 (t, 6H), 2.35 (s, 3H), 2.4 (s, 3H), 2.7 (q, 4H), 4.4 (d, 2H), 4.95 (bs, 1H), 6.15 (bs, 2H), 6.5 (s, 1H), 7.05–7.25 (m, 3H), 7.95 (s, 1H)

Example 1.13

Synthesis of 2,3-dimethyl-8-(2-methylbenzylamino)-imidazo[1,2-a]pyridine-6-carboxamide

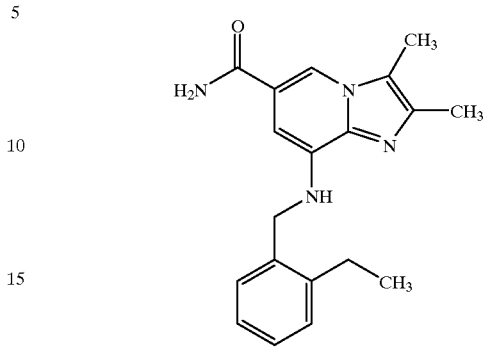

8-Amino-2,3-dimethylimidazo[1,2-a]pyridine-6-carboxamide mesylate (4.0 g, 10.7 mmol), 2-ethylbenzylchloride (1.65 g, 10.7 mmol), diisopropylethylamin (3.0 g, 23.3 mmol) in diemethylformamide (20 ml).

The title compound was prepared according to Example 1.12 (Yield: 1.15 g, 26%)

$^1$H-NMR (300 MHz, CDCl$_3$): δ1.2 (t, 3H), 2.3 (s, 3H), 2.35 (s, 3H), 2.75 (q, 2H), 4.5 (d, 2H), 6.3 (t, 1H), 6.4 (s, 1H), 7.05–7.25 (m, 4H), 7.3 (bs, 1H), 7.85 (bs, 1H), 8.05 (s, 1H)

Example 1.14

Synthesis of 2,3 dimethyl-8-(2-ethyl-6-methylbenzylamino)-N-hydroxyethyl-imidazo[1,2-a]pyridine-6-carboxamide

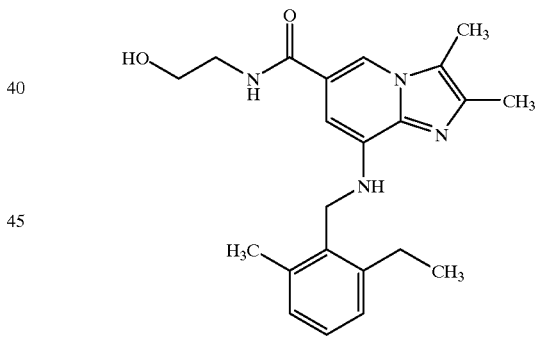

2,3-dimethyl-8-(2-ethyl-6-methylbenzylamino)-imidazo[1,2-a]pyridine-6-carboxylic acid (0.3 g, 0.88 mmol) and o-Benzotriazol-1-yl-N,N,N',N'-Tetramethyluronium tetrafluoroborate (TBTU)(0.29 g, 0.90 mmol) were added to methylene chloride (15 ml) and the mixture was stirred for 5 min. Ethanolamin (0.11 g, 1.8 mmol) was added and the reaction mixture was stirred at ambient temperature for 2 h. The solvent was evaporated under reduced pressure and the residue was purified by column chromatography on silica gel using methylene chloride:methanol (9:1) as eluent. Crystallization from diethyl ether gave 0.2 (59%) of the desired product.

$^1$H-NMR (500 MHz, CDCl$_3$): δ1.2 (t, 3H), 2.3 (s, 6H), 2.35 (s, 3H), 2.7 (q, 2H), 3.55–3.6 (m, 2H), 3.8–3.85 (m, 2H), 4.35 (d, 2H), 4.9 (t, 1H), 6.4 (s, 1H), 6.85 (t, 1H), 7.05–7.2 (m, 3H), 7.75 (s, 1H)

Example 1.15
Synthesis of N-(2,3-dihydroxypropyl)-2,3 dimethyl-8-(2-ethyl-6-methylbenzylamino)-[1,2-a]pyridine-6-carboxamide

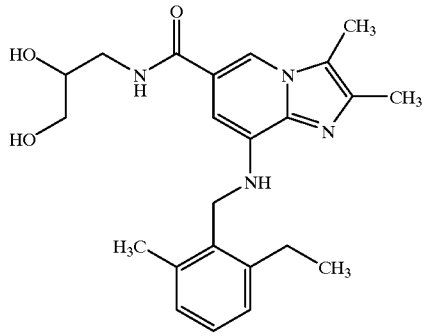

2,3-dimethyl-8-(2-ethyl-6-methylbenzylamino)-imidazo[1,2-a]pyridine-6-carboxylic acid (0.3 g, 0.88 mmol), o-Benzotriazol-1-yl-N,N,N',N'-Tetramethyluronium tetrafluoroborate (TBTU)(0.29 g, 0.90 mmol) and 3-amino-1,2-propanediol (0.16 g, 1.81 mmol) in dimethylformamide (10 ml).

The title compound was prepared according to Example 1.14 (Yield: 0.2 g, 54%)

$^1$H-NMR (500 MHz,CDCl$_3$): δ1,2 (t, 3H), 1.82–1.85 (m, 1H), 2.32 (s, 3H), 2.33 (s, 3H), 2.36 (s, 3H), 2.7 (q, 2H), 3.5–3.65 (m, 4H), 3.72–3.77 (m,1H), 3.85–3.91 (m,1H), 4.34 (d, 2H), 5.04 (t, 1H), 6.4 (d, 1H), 6.89 (t, 1H), 7.04–7.12 (m, 2H), 7.18 (t, 1H), 7.78 (d, 1H)

Example 1.16
Synthesis of 2,3 dimethyl-8-(2-ethyl-6-methylbenzylamino)-N-(2-methoxyethyl)imidazo[1,2-a]pyridine-6-carboxamide

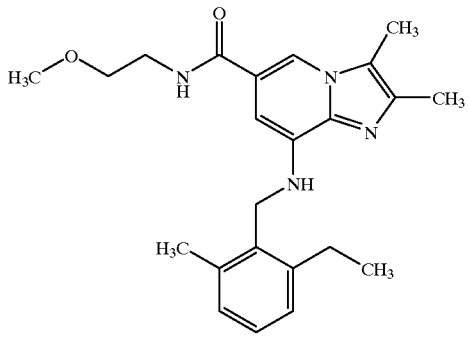

2,3-dimethyl-8-(2-ethyl-6-methylbenzylamino)-imidazo[1,2-a]pyridine-6-carboxylic acid (0.15 g, 0.44 mmol), o-Benzotriazol-1-yl-N,N,N',N'-Tetramethyluronium tetrafluoroborate (TBTU)(0.14 g, 0.44 mmol) and 2-methoxyethylamin (0.11 g, 1.4 mmol) in methylene chloride (10 ml).

The title compound were prepared according to Example 1.14

Crystallization from hexane:ethylacetate. (Yield: 0.09 g, 53%)

$^1$H-NMR (400 MHz,CDCl$_3$): δ1.22 (t, 3H), 2.34 (s, 3H), 2.38 (s, 3H), 2.39 (s, 3H), 2.71 (q, 2H), 3.42 (s, 3H), 3.6–3.72 (m, 4H), 4.38 (d, 2H), 4.91 (t, 1H), 6.42 (s, 1H), 6.58 (t, 1H), 7.04–7.2 (m, 3H), 7.88 (s, 1H)

Example 1.17
Synthesis of 2-methyl-8-(2-ethyl-6-methylbenzylamino)-imidazo[1,2-a]pyridine-6-carboxamide

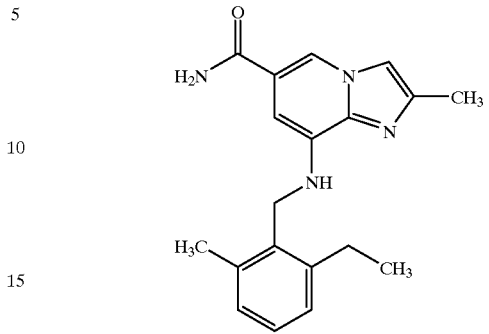

8-Amino-2-methylimidazo[1,2-a]pyridine-6-carboxamide (3.8 g, 20 mmol), 2-ethyl-6-methylbenzylchloride (2.8 g, 17 mmol), potassium carbonate (5.5 g, 40 mmol) and sodium iodide (0.1 g, 0.6 mmol) were added to dimethylformamide (75 ml) and the mixture was stirred at 50° C. for 4 h. and at room temperature for 48 h. The reaction mixture was filtered through silica gel and the gel was washed with methylene chloride. The solvents were evaporated under reduced pressure and the residue was purified by column chromatography on silica gel using methylene chloride:methanol (9:1) as eluent. Crystallization from a mixture of methylene chloride and hexane gave 0.13 g (2%) of the title compound.

$^1$H-NMR (400 MHz,CDCl$_3$): δ1.15 (t, 3H), 2.31 (s, 6H), 2.64 (q, 2H), 4.32 (d, 2H), 4.89 (bs, 1H), 6.36 (s, 1H), 7.0–7.15 (m, 3H), 7.23 (s, 3H), 8.03 (s, 1H)

Example 1.18
Synthesis of 2,3-dimethyl-8-(2-bromo-6-methylbenzylamino)-imidazo[1,2-a]pyridine-6-carboxamide

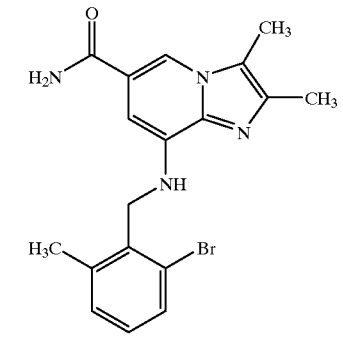

8-Amino-2,3-dimethylimidazo[1,2-a]pyridine-6-carboxamide mesylate (1.0 g, 5.0 mmol), 2-bromo-6-methylbenzylchloride (45%)(3.0 g, 5.0 mmol) and diisopropylethylamin (2.2 g, 17 mmol) were added to dimethylformamide (50 ml) and stirred at 50° C. for 48 h. Methylene chloride and water were added to the reaction mixture, the organic layer was separated, washed with saturated sodium chloride, dried (Na$_2$SO$_4$) and evaporated under reduced pressure. Purification of the residue twice by column chromatography on silica gel using methylene chloride:methanol (10:1) and ethylacetate as eluent gave 0.18 g (1%) of the desired product.

$^1$H-NMR (300 MHz,CDCl$_3$): δ2.28 (s, 3H), 2.30 (s, 3H), 2.36 (s, 3H), 4.48 (d, 2H), 5.0 (bs, 1H), 6.05 (bs, 2H), 6.41 (d, 1H), 6.95–7.1 (m, 2H), 7.37 (d, 1H), 7.87 (d, 1H)

Example 1.19
Synthesis of 2,3-dimethyl-8-(2-(2-hydroxyethyl)-6-methylbenzylamino)-imidazo[1,2-a]pyridine-6-carboxamide

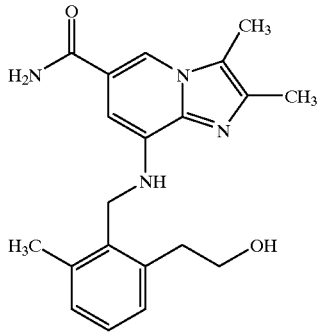

2,3-dimethyl-8-(2-(2-(benzyloxy)ethyl)-6-methylbenzylamino)-imidazo[1,2-a]pyridine-6-carboxamide (0.13 g, 0.29 mmol), cyclohexene (1 ml), Pd(OH)$_2$ cat. (25 mg) were added to ethanol (5 ml) and the mixture was refluxed overnight. An additional amount of cyclohexene (1 ml) and Pd(OH)$_2$ cat. (25 mg) were added and the mixture was refluxed for 4 h. The solvent was evaporated under reduced pressure and the residue was purified by column chromatography on silica gel using methylene chloride:methanol (9:1) as eluent. Treating the residue with chloroform and filtration gave 0.1 g (99%) of the title compound.

$^1$H-NMR (400 MHz, CD$_3$OD): δ2.29 (s, 3H), 2.40 (s, 3H), 2.42 (s, 3H), 2.94 (t, 2H), 3.74 (t, 2H), 4.47 (s, 2H), 6.83 (d, 1H), 711–7.20 (m, 3H), 8.12 (d, 1H)

Example 1.20
Synthesis of 8-(2-ethyl-6-methylbenzylamino)-N,N-bis(2-hydroxyethyl)-2,3-dimethylimidazo[1,2-a]pyridine-6-carboramide

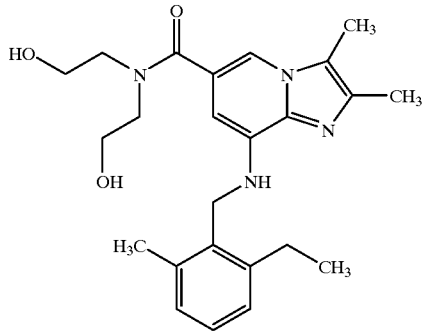

2,3-dimethyl-8-(2-ethyl-6-methylbenzylamino)-imidazo[1,2-a]pyridine-6-carboxylic acid (0.3 g, 0.88 mmol), o-Benzotriazol-1-yl-N,N,N',N'-Tetramethyluronium tetrafluoroborate (TBTU)(0.3 g, 0.94 mmol) and diethanolamine (0.2 g, 1.9 mmol) in methylene chloride (10 ml).

The title compound were prepared according to Example 1.14 (Yield: 0.19 g, 50%)

$^1$H-NMR (400 MHz,CDCl$_3$): ι1.2 (t, 3H), 2.3 (s, 3H), 2.35 (s, 3H), 2.4 (s, 3H), 2.7 (q, 2H), 3.65 (bs, 4H), 3.9 (bs, 4H), 4.35 (d, 2H), 4.95 (bs, 1H), 6.35 (s, 1H), 7.0–7.2 (m, 3H), 7.7 (s, 1H)

Example 1.21
Synthesis of 8-(2-ethyl-6-methylbenzylamino)-N-(2-hydroxyethyl)-N,2,3-trimethylimidazo[1,2-a]pyridine-6-carboxamide

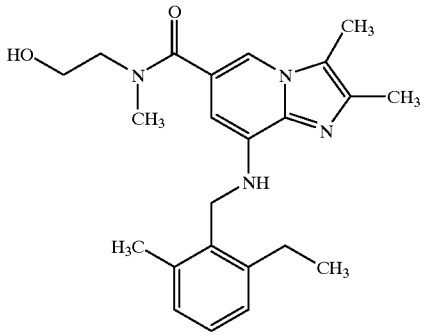

2,3-dimethyl-8-(2-ethyl-6-methylbenzylamino)-imidazo[1,2-a]pyridine-6-carboxylic acid (0.3 g, 0.88 mmol), o-Benzotriazol-1-yl-N,N,N',N'-Tetramethyluronium tetrafluoroborate (TBTU)(0.3 g, 0.94 mmol) and 2-(methylamino)ethanol (0.2 g, 2.66 mmol) in methylene chloride (10 ml).

The title compound were prepared according to Example 1.14 (Yield: 0.25 g, 71%)

$^1$H-NMR (600 MHz,CDCl$_3$): δ1.2 (t, 3H), 2.25 (s, 6H), 2.35 (s, 3H), 2.7 (q, 2H), 3.15 (s, 3), 3.65 (bs, 2H), 3.9 (bs, 2H), 4.35 (d, 2H), 5.0 (bs, 1H), 6.25 (bs, 1H), 7.0–7.25 (m., 3H), 7.45 (bs, 1H)

Example 1.22
Synthesis of 2,3-dimethyl-8-(2-ethyl-6-methylbenzyloxy)-imidazo[1,2-a]pyridine-6-carboxamide

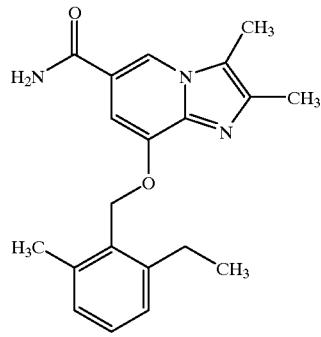

6-amino-5-(2-ethyl-6-methylbenzyloxy)nicotinamide (0.14 g, 0.49 mmol), 3-bromo-2-butanone (0.075 g, 0.49 mmol) and sodium bicarbonate (0.1 g, 1.2 mmol) was added to acetonitrile (3 ml) and was refluxed for 20 h. The solvent was evaporated under reduced pressure and the residue was purified by column chromatography on silica gel using methylene chloride:methanol (9:1) as eluent. Crystallization from acetonitrile gave 0.058 g (35%) of the title compound.

$^1$H-NMR (300 MHz,DMSO-d$_6$): δ1.14 (t, 3H), 2.24 (s, 3H), 2.33 (s, 3H), 2.40 (s, 3H), 2.69 (q, 2H), 5.25 (s, 2H), 7.1–7.3 (m, 4H), 7.51 (bs, 1H), 8.08 (bs, 1H), 8.42 (s, 1H)

2. PREPARATION OF INTERMEDIATES

Example 2.1
Synthesis of methyl 6-amino-5-nitronicotinate

6-Chloro-5-nitronicotinoyl chloride (22.0 g, 0.1 mol) was cooled to +5° C. Methanol was added dropwise during 30 min and the reaction mixture was stirred for 60 min. The temperature was not allowed to raise over +10° C. Ammonium hydroxide (25%, 400 ml) was added dropwise to the reaction mixture and the mixture was stirred at room temperature for 20 h. The product was filtered off, washed with water and dried to give 9.0 g (45.9%) of the title compound.

$^1$H-NMR (300 MHz, CDCl$_3$): δ3.95 (s, 3H), 6.3 (bs, 1H), 8.0 (bs, 1H), 8.95 (s, 1H), 9.05 (s, 1H)

Example 2.2
Synthesis of methyl 5,6-diaminonicotinate

Methyl 6-amino-5-nitronicotinate (9.0 g, 46 mmol) and a small amount of Pd/C cat. were added to methanol (200 ml) and the mixture was hydrogenated at room temperature and atmospheric pressure until the uptake of hydrogen ceased. Following filtration through celite, the methanol was evaporated under reduced pressure to give the title compound, 7.0 g (92%).

$^1$H-NMR (300 MHz, CDCl$_3$): δ3.3 (s, 2H), 3.9 (s, 3H), 4.75 (s, 2H), 7.45 (s, 1H), 8.35 (s, 1H)

Example 2.3
Synthesis of methyl 8-amino-2,3-dimethylimidazo[1,2-a]pyridine-6-carboxylate Methyl 5,6-diaminonicotinate (0.9 g, 5.4 mmol) and 3-bromo-2-butanon (0.9 g, 6.0 mmol) were added to acetonitril (30 ml) and refluxed for 24 h. Upon cooling some of the product was filtered off as hydrobromide salt. 20 ml of the filtrate was evaporated under reduced pressure and diethyl ether was added. More product was filtrated off as hydrobromide salt. The salt was dissolved in methylene chloride and washed with a bicarbonate solution. The organic layer was separated, dried over Na$_2$SO$_4$ and evaporated under reduced pressure to give 0.7 g (59%) of the desired compound.

$^1$H-NMR (300 MHz, CDCl$_3$): δ2.4 (s, 6H), 3.9 (s, 3H), 4.5 (s, 2H), 6.85 (s, 1H), 8.1 (s, 1H)

Example 2.4
Synthesis of methyl 2,3-dimethyl-8-(2-ethyl-6-methylbenzylamino)-imidazo[1,2-a]pyridine-6-carboxylate Methyl 8-amino-2,3-dimethylimidazo[1,2-a]pyridine-6-carboxylate (0.7 g, 3.2 mmol), 2-ethyl-6-methylbenzylchloride (0.54 g, 3.2 mmol), potassium carbonate (0.9 g, 6.4 mmol) and a cat. amount of potassium iodide were added to acetonitrile (20 ml) and were refluxed for 6 h. Following filtration, the acetonitrile was evaporated under reduced pressure to give an oil. The oily residue was solved in methylene chloride and washed with water. The organic layer was separated, dried over Na$_2$SO$_4$ and evaporated under reduced pressure to give a solid. Purification by column chromatography on silica gel using methylene chloride:ethylacetate (10:1) as eluent gave 0.42 g (38%) of the title compound.

$^1$H-NMR (500 MHz, CDCl$_3$): δ1.15 (t, 3H), 2.35 (s, 3H), 2.4 (s, 3H), 2.43 (s, 3H), 2.75 (q, 2H), 4.0 (s, 3H), 4.25 (d, 2H), 4.9 (bs, 1H), 6.8 (s,1H), 7.05–7.2 (m, 3H), 8.1 (s, 1H)

Example 2.5
Synthesis of 2,3-dimethyl-8-(2-ethyl-6-methylbenzylamino)-imidazo[1,2-a]pyridine-6-carboxylic acid Methyl 2,3-dimethyl-8-(2-ethyl-6-methylbenzylamino)-imidazo[1,2-a]pyridine-6-carboxylate (0.4 g, 1.1 mmol) was added to a mixture of 1,4-dioxane (6 ml) and 2 M NaOH (6 ml) and was refluxed for 30 min. The dioxane was evaporated under reduced pressure and the aqueous solution was made acidic by addition of 2 M HCl. The acidic aqueous was basified by the addition of a saturated bicarbonate solution and the solid that formed was isolated by filtration to give 0.35 g (91%) of the title compound.

$^1$H-NMR (400 MHz, DMSO-d$_6$): δ1.15 (t, 3H), 2.2 (s, 3H), 2.35 (s, 6H), 2.7 (q, 2H), 4.35 (d, 2H), 4.65 (t, 1H), 6.8 (s, 1H), 7.05–7.2 (m, 3H), 7.95 (s, 1H)

Example 2.6
Synthesis of ethyl 8-amino-2,3-dimethylimidazo[1,2-a]pyridine-6-carboxylate Ethyl 5,6-diaminonicotinate (1.4 g, 7.7 mmol) and 3-bromo-2-butanon (1.16 g, 7.2 mmol) were added to 1,2-dimethoxyethan (50 ml) and refluxed for 20 h. The solvent was evaporated under reduced pressure and the residue was dissolved in methylene chloride. The methylene chloride solution was washed with saturated sodium bicarbonate and dried (Na$_2$SO$_4$). The solvent was evaporated under reduced pressure and the residue was purified by column chromatography on silica gel using methylene chloride:methanol (10:1) as eluent to give 0.3 g (17%) of the title compound.

$^1$H-NMR (300 MHz, CDCl$_3$): δ1.4 (t, 3H), 2.4 (s, 6H), 4.35 (q, 2H), 4.6 (s, 2H), 6.75 (s, 1H), 8.2 (s, 1H)

Example 2.7
Synthesis of ethyl 2,3-dimethyl-8-(2-ethyl-6-methylbenzylamino)-imidazo[1,2-a]pyridine-6-carboxylate Ethyl 8-amino-2,3-dimethylimidazo[1,2-a]pyridine-6-carboxylate (0.7 g, 3.0 mmol), 2-ethyl-6-methylbenzylchloride (0.5 g, 3.0 mmol), sodium carbonate (0.64 g, 6.0 mmol) and a cat. amount of potassium iodide were added to acetone (50 ml) and were refluxed for 20 h. Following filtration, the acetone was evaporated under reduced pressure to give an oil. The oily product was purified by column chromatography on silica gel using diethyl ether:petroleum ether (1:1) as eluent to give 0.12 g (9%) of the title product.

$^1$H-NMR (500 MHz, CDCl$_3$): δ1.25 (t, 3H), 1.5 (t, 3H), 2.35 (s, 3H), 2.42 (s, 3H), 2.44 (s, 3H), 2.75 (q, 2H), 4.45–4.5 (m, 4H), 4.9 (bs, 1H), 6.8 (s, 1H), 7.05–7.2 (m, 3H), 8.1 (s, 1H)

Example 2.8
Synthesis of 6-amino-5-nitronicotinamide

A solution of 6-chloro-5-nitronicotinoyl chloride (38 g, 0.2 mol) in tetrahydrofuran (500 ml) was stirred at +5° C. and ammonia was bubbled into the solution. After 1 h the reaction mixture was allowed to warm to room temperature and ammonia was bubbled into the solution for additional 2.5 h. The reaction mixture was stirred at room temperature for 20 h. The solids were removed by filtration, washed thoroughly with water and were dried under reduced pressure to give 18.5 g (51%) of the title compound.

$^1$H-NMR (400 MHz, DMSO-d$_6$): δ7.4 (s, 1H), 8.05 (s, 1H), 8.3 (s, 2H), 8.8 (s, 2H)

Example 2.9
Synthesis of 5,6-diaminonicotinamide

A suspension of 6-amino-5-nitronicotinamide (18 g, 99 mmol) and a cat. amount of Pd/C in methanol (600 ml) and the mixture was hydrogenated at room temperature and atmospheric pressure until the uptake of hydrogen ceased. Following filtration through celite, the methanol was evaporated under reduced pressure to give the title compound, 14.5 g (96%).

$^1$H-NMR (300 MHz, DMSO-d$_6$): δ5.0 (bs, 2H), 6.1 (bs, 2H), 6.9 (bs, 1H), 7.15 (s, 1H), 7.55 (bs, 1H), 7.9 (s, 1H)

Example 2.10
Synthesis of 8-amino-2,3-dimethylimidazo[1,2-a]pyridine-6-carboxamide 5,6-Diaminonicotinamide (12.5 g, 82 mmol), 3-bromo-2-butanon (13.6, 90 mmol) and acetonitrile (150 ml) were refluxed for 20 h. Additional 3-bromo-2-butanon (4.0 g, 26.5 mmol) was added and the reaction mixture was refluxed for 5 h. Upon cooling the solids were removed by filtration. The solids were added to methylene chloride (150 ml), methanol (150 ml) and potassium carbonate (22 g, 160 mmol) and were stirred for 30 min. The solids were removed by filtration and evaporation of the solvents under reduced pressure gave an oily residue. Purification by column chromatography on silica gel eluting with methylene chloride:methanol (5:1) gave 3.3 g (20%) of the title compound.
$^1$H-NMR (400 MHz, DMSO-$d_6$): δ2.25 (s, 3H), 2.35 (s, 3H), 5.6 (s, 2H), 6.65 (s, 1H), 7.15 (bs, 1H), 7.85 (bs, 1H), 8.05 (s, 1H)

Example 2.11
Synthesis of ethyl 8-amino-6-(aminocarbonyl)-2-methylimidazo[1,2-a]pyridine-3-carboxylate 5,6-Diaminonicotinamide (2.0 g, 13.4 mmol), ethyl-2-chloroacetoacetate (2.38 g, 14.4 mmol) and ethanol (40 ml) were refluxed for 20 h. The precipitate was isolated by filtration and washed with ethanol and diethyl ether. The solids were suspended in water, basified with a sodium hydroxide solution and isolated by filtration. Washing the solids with water and diethyl ether gave 0.42 g (12%) of the desired product.
$^1$H-NMR (500 MHz, DMSO-$d_6$): δ1.4 (t, 3H), 2.6 (s, 3H), 4.35 (q, 2H), 5.95 (bs, 2H), 6.9 (s, 1H), 7.35 (bs, 1H), 8.0 (bs, 1H), 9.0 (s, 1H)

Example 2.12
Synthesis of ethyl 6-(aminocarbonyl)-8-(2-ethyl-6-methylbenzylamino)-2-methylimidazo[1,2-a]pyridine-3-carboxylate Ethyl 8-amino-6-(aminocarbonyl)-2-methylimidazo[1,2-a]pyridine-3-carboxylate (0.41 g, 1.6 mmol), 2-ethyl-6-methylbenzylchloride, sodium carbonate (0.7 g, 6.6 mmol), sodium iodide (0.15 g, 1.0 mmol) and acetone (20 ml) were refluxed for 44 h. Methylene chloride was added and the solids were removed by filtration. The filtrate was evaporated under reduced pressure and purification of the residue by column chromatography on silica gel eluting with methylene chloride:methanol (100:4) gave 0.35 g (56%) of the title compound. $^1$H-NMR (300 MHz, CDCl$_3$): δ1.25 (t, 3H), 1.45 (t, 3H), 2.35 (s, 3H), 3.65 (s, 3H), 2.7 (q, 2H), 4.4–4.45 (m, 4H), 5.0 (t, 1H), 6.95 (s, 1H), 7.0–7.2 (m, 3H), 9.2 (s, 1H)

Example 2.13
Synthesis of 8-amino-2-methylimidazo[1,2-a]pyridine-6-carboxamide mesylate 5,6-diaminonicotinamide (10 g, 66 mmol), chloroacetone (6.1 g, 66 mmol) and sodium bicarbonate (11.2 g, 132 mmol) were added to dimethylformamide (200 ml) and the mixture was stirred for 72 h. at room temperature. Most of the solvent was evaporated under reduced pressure and methanesulfonic acid (6 g, 63 mmol) was added. More solvent was evaporated under reduced pressure and ethanol was added to the residue. Upon warming the mixture to 60° C. the product crysstallized as salt and was filtred off to give 6 g (32%) of the title compound.
$^1$H-NMR (400 MHz,CDCl$_3$): δ2.3 (s, 6H), 7.25 (s,1H), 7.4 (s, 1H), 7.6 (s, 1H), 7.75 (s, 1H), 7.85 (s, 1H), 7.9 (s, 1H), 8.15 (s,1H), 8.6 (s, 1H)

Example 2.14
Synthesis of 1-bromo-2-isopropyl-6-methylbenzene 2-isopropyl-6-methylanilin (14.9 g, 0.1 mol) was solved in conc hydrobromic acid (40 ml) and the mixture was cooled to 5° C. Sodium nitrite (7.0 g, 0.1 mol) in water (15 ml) was added so that the temperature was below 10° C. A solution of copper(I)bromide in conc hydrobromic acid (10 ml) was added to the reaction mixture and the temperature was allowed to raise to room temperature. The mixture was stirred for 1 h. at room temperature and 30 min at 40° C. Hexane was added and the organic layer was separated and evaporated under reduced pressure. Purification by column chromatography on silica gel using hexane as eluent gave 6.9 g (32%) of the title compound as an oil.
$^1$H-NMR (300 MHz,CDCl$_3$): δ1.23 (d, 6H), 2.43 (s, 3H), 3.4–3.55 (m, 1H), 7.05–7.2 (m, 3H)

Example 2.15
Synthesis of 2-isopropyl-6-methylbenzaldehyd

To a solution of 1-bromo-2-isopropyl-6-methylbenzene (6.9 g, 32.4 mmol) in diethyl ether (50 ml) was added magnesium turnings (0.9 g, 37 mmol) and the mixture was refluxed in nitrogen atmosphere until the reaction was started and was then stirred overnight at room temperature. Dimethylformamide (4 ml) was added dropwise during 10 min. and the mixture was stirred for 30 min. Saturated ammmoniumchloride solution (30 ml) was added and the mixture was stirred for 1 h. The organic layer was separated, filtrated and evaporated under reduced pressure. Purification by column chromatography on silica gel using hexane:methylene chloride (3:2) as eluent gave 1.75 g (33%) of the title compound .
$^1$H-NMR (500 MHz,CDCl$_3$): δ1.25 (d, 6H), 2.55 (s, 3H), 3.7–3.8 (m, 1H), 7.1–7.4 (m, 3H), 10.65 (s, 1H)

Example 2.16
Synthesis of 2-isopropyl-6-methylbenzylalcohol

To a solution of 2-isopropyl-6-methylbenzaldehyd (1.75 g, 10.8 mmol) in methanol (15 ml) was added sodium borohydride (0.35 g, 9.5 mmol) and the mixture was stirred 1 h. at room temperature. The solvent was evaporated under reduced pressure and to the residue was added hexane and water. The organic layer was separated and evaporated under reduced pressure to give 1.73 g (98%) of the title compound as an oil.
$^1$H-NMR (500 MHz,CDCl$_3$): δ1.25 (d, 6H), 2.45 (s, 3H), 3.3–3.4 (m, 1H), 4.8 (s, 2H), 7.05–7.2 (m, 3H)

Example 2.17
Synthesis of 2-isopropyl-6-methylbenzylchloride

To a solution of 2-isopropyl-6-methylbenzylalcohol (1.7 g, 10.4 mmol) in methylene chloride (20 ml) was added thionyl chloride (1.7 g, 14 mmol) and the reaction was stirred for 1 h. at room temperature. The solvent was evaporated under reduced pressure and the residue was filrated through silica gel using methylenechloride as eluent. The solvent was evaporated under reduced pressure to give 1.83 g (96%) of the title compound as an oil.
$^1$H-NMR (500 MHz,CDCl$_3$): δ1.25 (d, 6H), 2.45 (s, 3H), 3.25–3.35 (m, 1H), 4.75 (s, 2H), 7.05–7.25 (m, 3H)

Example 2.18
Synthesis of 2-bromo-6-methylbenzylbromide

A mixture of 3-bromo-o-xylene (15 g, 81 mmol), N-bromo succinimid (15.1 g, 85.1 mmol), dibenzoylperoxid (0.65 g) and tetrachloromethane (150 ml) was refluxed for 5 hours. After filtration the filtrate was washed with sodium hydrogensulfite and water. The organic layer was dried over

Example 2.19
Synthesis of 2-(2-bromo-3-methylphenyl)acetonitril 2-bromo-1-(bromomethyl)-3-methylbenzene (15 g, 0.057 mmol) and potassium cyanide (9.6 g, 0.148 mol) were added to dimethylformamide (75 ml) and stirred at 90° C. overnight. The solvent was evaporated under reduced pressure and the residue partitioned between water (150 ml) and methylene chloride. The aqueous layer was extracted twice with methylene chloride, the organic extracts was separated, washed twice with water and was evaporated under reduced pressure. Purification of the residue by column chromatography on silica gel using heptane:methylene chloride (3:7) as eluent gave 8.0 g (67%) of the title compound.

$^1$H-NMR (500 MHz,CDCl$_3$): δ2.44 (s, 3H), 3.86 (s, 2H), 7.22–7.37 (m, 3H)

Example 2.20
Synthesis of 2-(2-bromo-3-methylphenyl)acetic acid 2-(2-bromo-3-methylphenyl)acetonitril (8.0 g, 0.038 mol) was added to a mixture of water (60 ml) and sulfuric acid (50 ml) and the mixture was refluxed overnight. After cooling to room temperature water (200 ml) was added and the mixture was extracted twice with methylene chloride. The methylene chloride extracts were combined, washed twice with water, dried and evaporated under reduced pressure to give 7.9 g (90.8%) of the title compound.

$^1$H-NMR (400 MHz,CDCl$_3$): δ2.42 (s, 3H), 3.86 (s, 2H), 7.09–7.18 (m, 3H)

Example 2.21
Synthesis of ethyl 2-(2-bromo-3-methylphenyl)acetate 2-(2-bromo-3-methylphenyl)acetic acid (7.9 g, 0.034 mol) and sulfuric acid (0.1 ml) were added to ethanol (25 ml) and the mixture was refluxed overnight. The solvent was evaporated and to the residue was added saturated sodium carbonate. The aqueous solution was extracted twice with diethyl ether, the organic extracts were combiened, washed twice with water, dried and evaporated under reduced pressure to give the desired product as an oil. (8.5 g,97.7%).

$^1$H-NMR (400 MHz,CDCl$_3$): δ1.24 (t, 3H), 2.40 (s, 3H), 3.78 (s, 3H), 4.16 (q,2H), 7.06–7.14 (m, 3H)

Example 2.22
Synthesis of 2-(2-bromo-3-methylphenyl)-1-ethanol

LiAlH4 (3.1 g, 0.083 mol) was suspended in dry tetrahydrofuran (100 ml) in argon atmosphere. Ethyl 2-(2-bromo-3-methylphenyl)acetate (8.5 g, 0.033 mol) solved in dry tetrahydrofuran (50 ml) was added and the mixture was stirred at room temperature for 4 h. The mixture was cooled on ice and 3.1 ml of water was added dropwise, followed by 3.1 ml of 15% sodium hydroxide and then 9.3 ml of water. After 15 h. the solids were removed by filtration and washed thoroughly with tetrahydrofuran. The filtrate was removed under reduced pressure. Purification of the residue by filtrating through silica gel using methylene chloride:methanol (9:1) as eluent gave 7.0 g (98.6%) of the title compound as an oil.

$^1$H-NMR (400 MHz,CDCl$_3$): δ2.39 (s, 3H), 3.00 (t, 2H), 3.81 (t, 2H), 7.04–7.10 (m, 3H)

sodium sulfate and evaporated in vacuo. Chromatography (SiO$_2$) (petroleum ether:ethyl acetate, 100:4) gave a 16.8 g fraction of a mixture containing 45% of the title compound. This mixture was used without further purification.

$^1$H-NMR (300 MHz,CDCl$_3$): δ2.5 (s, 3H), 4.65 (s, 2H), 7.05–7.45 (m, 3H)

Example 2.23
Synthesis of benzyl 2-bromo-3-methylphenethyl ether

Sodium hydride (50% in oil) (1.7 g, 0.036 mol) was suspended in dry tetrahydrofuran (75 ml) in argon atmosphere. 2-(2-bromo-3-methylphenyl)-1-ethanol (7.0 g, 0.033 mol) solved in tetrahydrofuran (25 ml) was added dropwise during 30 min at room temperature. Benzyl bromide (6.2 g, 0.036 mol) was added and the reaction mixture was stirred at room temperature over night. Water (1.0 ml) was added carefully and the solvent was evaporated under reduced pressure. The residue was partitioned between water and diethyl ether and the water layer was extracted twice with diethyl ether. The ether extracts were combined, washed twice with water, and evaporated under reduced pressure. Purification of the residue by column chromatography on silica gel using heptane:methylene chloride (7:3) as eluent gave 7.5 g (74.3%) of the title compound.

$^1$H-NMR (400 MHz,CDCl$_3$): δ2.38 (s, 3H), 3.10 (t, 2H), 3.69 (t, 2H), 4.51 (s, 2H), 7.04–7.08 (m, 3H), 7.21–7.30 (m, 5H)

Example 2.24
Synthesis of 2-[2-(benzyloxy)ethyl]-6-methylbenzaldehyde

To a solution of benzyl 2-bromo-3-methylphenethyl ether (3.2 g, 0.0105 mol) in dry tetrahydrofuran in a nitrogen atmosphere at −65° C. was added tert-butyllithium (1.7 M in pentane)(10.5 ml, 0.018 mol) and the mixture was stirred at −20° C. for 30 min. Dimethylformamide (1.5 g, 0.021 mol) was added dropwise at −65° C. and the mixture was stirred at −20° C. for 30 min and at room temperature for 1 h. To the solution was water added carefully and 2M HCl to make it acidic and the mixture was stirred for 30 min. To the mixture was added diethyl ether (50 ml), the organic layer was separated, washed with saturated sodium carbonate and water. The organic layer was separated, dried and evaporated under reduced pressure. Purification of the residue by column chromatography on silica gel using heptane:methylene chloride (2:8) as eluent gave 1.0 g (38.5%) of the title compound.

$^1$H-NMR (300 MHz,CDCl$_3$): δ2.55 (s, 3H), 3.23 (t, 2H), 3.66 (t, 2H), 4.46 (s, 2H), 7.05–7.31 (m, 8H), 10.54 (s, 1H)

Example 2.25
Synthesis of 8-((2-[2-(benzyloxy)ethyl]-6-methylbenzyl)amino)-2,3-dimethylimidazo[1,2-a]pyridine-6-carboxamide To a solution of 8-Amino-2,3-dimethylimidazo[1,2-a]pyridine-6-carboxamide mesylate 1.4 g (0.0038 mol) in methanol (20 ml) in a nitrogen atmosphere was added zinc chloride (1.0 g, 0.0039 mol) solved in methanol(10 ml) and the mixture was stirred for 30 min. To the mixture were added 2-[2-(benzyloxy)ethyl]-6-methylbenzaldehyde (1.0 g, 0.0039 mol) and sodium cyano borohydride (0.48 g, 0.0076 mol) and the mixture was refluxed overnight. The reation mixture was cooled to room temperature, triethylamine (4 ml) was added, the mixture was stirred for 30 min, and the solvent was evaporated under reduced pressure. The residue was purified by column chromatography on silica gel using methylene chloride:methanol (9:1) as eluent. The residue was solved in diethyl ether, treated with diethyl ether/HCl and the precipitated product as HCl salt was filtered off. The salt was soloved in methylene chloride and washed with saturated sodium carbonate. The organic layer was separated, washed with water, dried and evaporated under reduced pressure to give 0.13 g (7.7 g) of the title compound.

$^1$H-NMR (300 MHz,CDCl$_3$): δ2.31 (s, 3H), 2.33 (s, 3H), 2.34 (s, 3H), 2.98 (t, 2H), 3.66 (t, 2H), 4.37 (d, 2H), 4.46 (s, 2H), 5.02 (bs, 1H), 6.29 (bs, 2H), 6.47 (s, 1H), 7.03–7.26 (m, 8H), 7.91 (s, 1H)

Example 2.26
Synthesis of 2-ethyl-6-methylbenzyl 5-(2-ethyl-6-methylbenzyloxy)-6-nitronicotinate 5-hydroxy-6-nitronicotinic acid (1 g, 5 mmol), 2-ethyl-6-methylbenzylchloride (1.85 g, 11 mmol), N,N-diisopropylamine (1.75 g, 14 mmol) and tetrabutylammonium iodide (0.1 g) was added to acetonitrile (10 ml) and was refluxed for 3 h. The solvent was evaporated under reduced pressure and the residue was solved in methylene chloride and washed with water. The organic layer was separated, dried and evaporated under reduced pressure. Purification of the residue by column chromatograhy on silica gel using n-hexane:methylene chloride (1:1) as eluent gave 0.7 g (29%) of the title compound.

$^1$H-NMR (300 MHz,CDCl$_3$): δ1.2 (t, 3H), 1.25 (t, 3H), 2.35 (s, 3H), 2.45 (s, 3H), 2.7 (q, 2H), 2.8 (q, 2H), 5.25 (s, 2H), 5.55 (s, 2H), 7.05–7.3 (m, 6H), 8.2 (s, 1H),

Example 2.27
Synthesis of 6-amino-5-(2-ethyl-6-methylbenzyloxy) nicotinamide 2-ethyl-6-methylbenzyl 5-(2-ethyl-6-methylbenzyloxy)-6-nitronicotinate (0.7 g, 2 mmol) was added to a solution of ammonia in methanol (5–10%)(40 ml) and the mixture was stirred at 35° C. for 96 h. The solvent was evaporated under reduced pressure. Purification of the residue twice by column chromatography on silica gel using ethylacetate:methylene chloride (1:1) and methanol:methylene chloride (1:9) as eluent gave 0.14 g (31%) of the title compound.

$^1$H-NMR (500 MHz,CDCl$_3$): δ1.21 (t, 3H), 1.87 (s, 2H), 2,37 (s, 3H), 2.72 (q, 2H), 5.11 (s, 2H), 5.99 (bs, 2H), 7.1–7.3 (m, 3H), 7.67 (d, 1H), 8.09 (d, 1H)

BIOLOGICAL TESTS
1. In vitro Experiments
Acid Secretion Inhibition in Isolated Rabbit Gastric Glands Inhibiting effect on acid secretion in vitro in isolated rabbit gastric glands was measured as described by Berglindh et al. (1976) Acta Physiol. Scand. 97, 401–414.
Determination of H$^+$,K$^+$-ATPase Activity Membrane vesicles (2.5 to 5 μg) were incubated for 15 min at +37° C. in 18 mM Pipes/Tris buffer pH 7.4 containing 2 mM MgCl$_2$, 10 mM KCl and 2 mM ATP. The ATPase activity was estimated as release of inorganic phosphate from ATP, as described by LeBel et al. (1978) Anal. Biochem. 85, 86–89.

2. In vivo Experiments
Inhibiting Effect on Acid Secretion in Female Rats

Female rats of the Sprague-Dawly strain are used. They are equipped with cannulated fistulae in the stomach (lumen) and the upper part of the duodenum, for collection of gastric secretions and administration of test substances, respectively. A recovery period of 14 days after surgery is allowed before testing commenced.

Before secretory tests, the animals are deprived of food but not water for 20 h. The stomach is repeatedly washed through the gastric cannula with tap water (+37° C.), and 6 ml Ringer-Glucose given subcutaneously. Acid secretion is stimulated with infusion during 2.5–4 h (1.2 ml/h, subcutaneously) of pentagastrin and carbachol (20 and 110 nmol/kg. h, respectively), during which time gastric secretions are collected in 30-min fractions. Test substances or vehicle are given either at 60 min after starting the stimulation (intravenous and intraduodenal dosing, 1 ml/kg), or 2 h before starting the stimulation (oral dosing, 5 ml/kg, gastric cannula closed). The time interval between dosing and stimulation may be increased in order to study the duration of action. Gastric juice samples are titrated to pH 7.0 with NaOH, 0.1 M, and acid output calculated as the product of titrant volume and concentration.

Further calculations are based on group mean responses from 4–6 rats. In the case of administration during stimulation; the acid output during the periods after administration of test substance or vehicle are expressed as fractional responses, setting the acid output in the 30-min period preceding administration to 1.0. Percentage inhibition is calculated from the fractional responses elicited by test compound and vehicle. In the case of administration before stimulation; percentage inhibition is calculated directly from acid output recorded after test compound and vehicle.
Bioavailability in Rat Adult rats of the Sprague-Dawley strain are used. One to three days prior to the experiments all rats are prepared by cannulation of the left carotid artery under anaesthesia. The rats used for intravenous experiments are also cannulated in the jugular vein (Popovic (1960) J. Appl. Physiol. 15, 727–728). The cannulas are exteriorized at the nape of the neck.

Blood samples (0.1–0.4 g) are drawn repeatedly from the carotid artery at intervals up to 5.5 hours after given dose. The samples are frozen until analysis of the test compound.

Bioavailability is assessed by calculating the quotient between the area under blood/plasma concentration (AUC) curve following (i) intraduodenal (i.d.) or oral (p.o.) administration and (ii) intravenous (i.v.) administration from the rat or the dog, respectively.

The area under the blood concentration vs. time curve, AUC, is determined by the log/linear trapezoidal rule and extrapolated to infinity by dividing the last determined blood concentration by the elimination rate constant in the terminal phase. The systemic bioavailability (F %) following intraduodenal or oral administration is calculated as $$F(\%)=(AUC\ (p.o.\ or\ i.d.)/AUC\ (i.v.))\times 100.$$

Inhibition of Gastric Acid Secretion and Bioavailability in the Conscious Dog

Labrador retriever or Harrier dogs of either sex are used. They are equipped with a duodenal fistula for the administration of test compounds or vehicle and a cannulated gastric fistula or a Heidenhaim-pouch for the collection of gastric secretion.

Before secretory tests the animals are fasted for about 18 h but water is freely allowed. Gastric acid secretion is stimulated for up to 6.5 h infusion of histamine dihydrochloride (12 ml/h) at a dose producing about 80% of the individual maximal secretory response, and gastric juice collected in consecutive 30-min fractions. Test substance or vehicle is given orally, i.d. or i.v., 1 or 1.5 h after starting the histamine infusion, in a volume of 0.5 ml/kg body weight. In the case of oral administration, it should be pointed out that the test compound is administered to the acid secreting main stomach of the Heidenham-pouch dog.

The acidity of the gastric juice samples are determined by titration to pH 7.0, and the acid output calculated. The acid output in the collection periods after administration of test substance or vehicle are expressed as fractional responses, setting the acid output in the fraction preceding administration to 1.0. Percentage inhibition is calculated from fractional responses elicited by test compound and vehicle.

Blood samples for the analysis of test compound concentration in plasma are taken at intervals up to 4 h after dosing. Plasma is separated and frozen within 30 min after collection and later analyzed. The systemic bioavailability (F %) after oral or i.d. administration is calculated as described above in the rat model.

What is claimed is:
1. A compound of the formula I

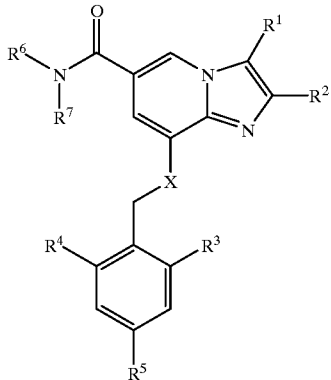

or a pharmaceutically acceptable salt thereof, wherein
$R^1$ is
(a) H,
(b) $CH_3$, or
(c) $CH_2OH$;
$R^2$ is
(a) $CH_3$ or
(b) $CH_2CH_3$;
$R^3$ is
(a) H,
(b) $C_1$–$C_6$ alkyl,
(c) hydroxylated $C_1$–$C_6$ alkyl or
(d) halogen;
$R^4$ is
(a) H,
(b) $C_1$–$C_6$ alkyl,
(c) hydroxylated $C_1$–$C_6$ alkyl, or
(d) halogen;
$R^5$ is
(a) H, or
(b) halogen;
$R^6$ and $R^7$ are the same or different and selected from
(a) H,
(b) $C_1$–$C_6$ alkyl,
(c) hydroxylated $C_1$–$C_6$ alkyl, or
(d) $C_1$–$C_6$ alkoxy-substituted $C_1$–$C_6$ alkyl; and
X is
(a) NH, or
(b) O.
2. A compound according to claim 1 wherein $R^1$ is $CH_3$ or $CH_2OH$; $R^2$, $R^3$ and $R^4$ independently are $CH_3$ or $CH_2CH_3$; and $R^5$ is H, Br, Cl, or F.
3. The compound according to claim 1 which is
2,3-dimethyl-8-(2-ethyl-6-methylbenzylamino)-N-propylimidazo[1,2-a]pyridine-6-carboxamide,
8-(2-ethyl-6-methylbenzylamino)-3-hydroxymethyl-2-methylimidazo[1,2-a]pyridine-6-carboxamide,
2,3-dimethyl-8-(2,6-dimethylbenzylamino)-N-hydroxyethylimidazo[1,2-a]pyridine-6-carboxamide,
2,3-dimethyl-8-(2-ethyl-6-methylbenzylamino)-imidazo[1,2-a]pyridine-6-carboxamide,
8-(2-ethyl-6-methylbenzylamino)-N,2,3-trimethylimidazo[1,2-a]pyridine-6-carboxamide,
8-(2-ethyl-6-methylbenzylamino)-N,N,2,3-tetramethylimidazo[1,2-a]pyridine-6-carboxamide,
2,3-dimethyl-8-(2,6-dimethylbenzyl-amino)-imidazo[1,2-a]pyridine-6-carboxamide,
2,3-dimethyl-8-(2-ethyl-4-fluoro-6-methylbenzylamino)-imidazo[1,2-a]pyridine-6-carboxamide mesylate,
2,3-dimethyl-8-(2-methylbenzylamino)-imidazo[1,2-a]pyridine-6-carboxamide,
2,3-dimethyl-8-(2,6-dimethyl-4-fluoro-benzylamino)-imidazo[1,2-a]pyridine-6-carboxamide mesylate,
2,3-dimethyl-8-(2-methyl-6-isopropylbenzylamino)-imidazo[1,2-a]pyridine-6-carboxamide mesylate,
2,3-dimethyl-8-(2,6-diethyl-benzylamino)-imidazo[1,2-a]pyridine-6-carboxamide,
2,3-dimethyl-8-(2-ethylbenzylamino)-imidazo[1,2-a]pyridine-6-carboxamide,
2,3 dimethyl-8-(2-ethyl-6-methyl-benzylamino)-N-hydroxyethyl-imidazo[1,2-a]pyridine-6-carboxamide,
N-(2,3-dihydroxypropyl)-2,3 dimethyl-8-(2-ethyl-6-methylbenzylamino)-[1,2-a]pyridine-6-carboxamide,
2,3 dimethyl-8-(2-ethyl-6-methyl-benzylamino)-N-(2-methoxyethyl)-imidazo[1,2-a]pyridine-6-carboxamide,
2-methyl-8-(2-ethyl-6-methylbenzylarnino)-imidazo[1,2-a]pyridine-6-carboxamide,
2,3-dimethyl-8-(2-bromo-6-methylbenzylaniino)-imidazo[1,2-a]pyridine-6-carboxamide,
2,3-dimethyl-8-(2-(2-hydroxyethyl)-6-methylbenzylamino)-imidazo[1,2-a]pyridine-6-carboxamide,
8-(2-ethyl-6-methylbenzylamino)-N,N-bis(2-hydroxyethyl)-2,3-dimethylimidazo[1,2-a]pyridine-6-carboxamide,
8-(2-ethyl-6-methylbenzylamino)-N-(2-hydroxyethyl)-N,2,3-trimethylimidazo[1,2-a]pyridine-6-carboxamide,
2,3-dimethyl-8-(2-ethyl-6-methylbenzyloxy)-imidazo[1,2-a]pyridine-6-carboxamide, or
a pharmaceutically acceptable salt thereof.
4. The compound according to claim 1 which is
8-(2-ethyl-6-methylbenzylamino)-3-hydroxymethyl-2-methylimidazo[1,2-a]pyridine-6-carboxamide,
2,3-dimethyl-8-(2,6-dimethylbenzylamino)-N-hydroxyethyl-imidazo[1,2-a]pyridine-6-carboxamide,
2,3-dimethyl-8-(2-ethyl-6-methylbenzylamino)-imidazo[1,2-a]pyridine-6-carboxamide,
8-(2-ethyl-6-methylbenzylamino)-N,2,3-trimethylimidazo[1,2-a]pyridine-6-carboxamide,
2,3-dimethyl-8-(2,6-dimethylbenzylamino)-imidazo[1,2-a]pyridine-6-carboxamide,
2,3-dimethyl-8-(2-ethyl-4-fluoro-6-methylbenzylamino)-imidazo[1,2-a]pyridine-6-carboxamide,
2,3-dimethyl-8-(2,6-dimethyl-4-fluoro-benzylamino)-imidazo[1,2-a]pyridine-6-carboxamide,
2,3-dimethyl-8-(2,6-diethylbenzylamino)-imidazo[1,2-a]pyridine-6-carboxamide,
2,3 dimethyl-8-(2-ethyl-6-methylbenzylamino)-N-hydroxyethylimidazo[1,2-a]pyridine-6-carboxamide,
2,3 dimethyl-8-(2-ethyl-6-methylbenzylamino)-N-(2-methoxyethyl)-imidazo[1,2-a]pyridine-6-carboxamide, or
a pharmaceutically acceptable salt thereof.
5. A compound according to claim 1 as a hydrochloride or mesylate salt.
6. A product containing at least one compound according to any one of claims 1–5 and at least one antimicrobial agent as a combined preparation for simultaneous, separate or sequential use in the prevention or treatment of gastrointestinal inflammatory diseases.
7. A product containing at least one compound according to any one of claims 1–5 and at least one proton pump inhibitor as a combined preparation for simultaneous, separate or sequential use in the prevention or treatment of gastrointestinal inflammatory diseases.

8. A process for the preparation of a compound according to any one of claims 1 to 5, wherein X is NH, comprising (a) reacting a compound of the Formula II

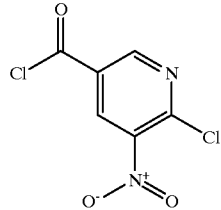

II with a compound of the Formula III

III wherein $R^6$ and $R^7$ are as defined in claim 1, in an inert solvent, to produce a compound of the Formula IV,

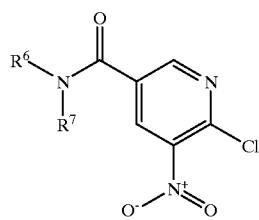

IV (b) reacting a compound of the Formula IV wherein $R^6$ and $R^7$ are as defined in claim 1, with ammonia in an inert solvent to produce a compound of the Formula V

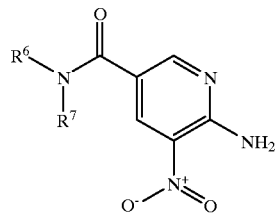

V (c) reducing a compound of the Formula V wherein $R^6$ and $R^7$ are as defined in claim 1 in an inert solvent under standard conditions to produce a compound of the Formula VI

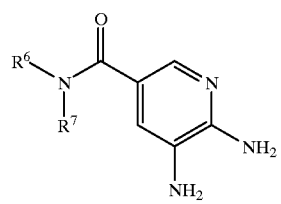

VI (d) reacting a compound of the Formula VI wherein $R^6$ and $R^7$ are as defined in claim 1 with a compound of Formula VII

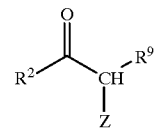

VII wherein $R^2$ is as defined in claim 1, Z is a leaving group and $R^9$ represent H, $CH_3$ or an ester group, in an inert solvent with or without a base to produce a compound of the Formula VIII

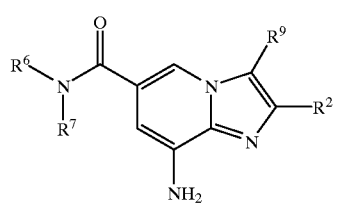

VIII (e) reacting a compound of the Formula VIII wherein $R^6$, $R^7$ and $R^2$ are as defined in claim 1, and $R^9$ is H, $CH_3$ or an ester group with a compound of Formula IX

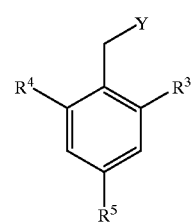

IX wherein $R^3$, $R^4$, and $R^5$ are as defined in claim 1, and Y is a leaving group in an inert solvent with or without a base, to produce a compound of the Formula X

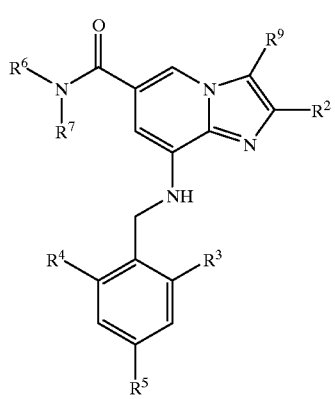

X (f) reducing a compound of Formula X wherein $R^9$ is an ester group in an inert solvent to produce a compound of the Formula I wherein $R^1$ is $CH_2OH$ and X is NH.

9. A process for the preparation of a compound according to any one of claims 1 to 5, wherein X is NH and $R^1$ is H or $CH_3$, comprising (a) reacting a compound of the Formula II

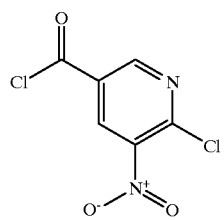

II with an alcohol compound of the general formula $R^{10}$—OH, wherein $R^{10}$ is an alkyl group under standard conditions, to produce a compound of the Formula XI

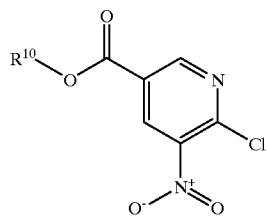

XI (b) reacting a compound of the Formula XI wherein $R^{10}$ is an alkyl group, with ammonia in an inert solvent under standard conditions to produce a compound of the Formula XII

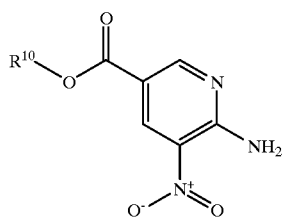

XII (c) reducing a compound of the Formula XII wherein $R^{10}$ is an alkyl group in an inert solvent under standard conditions to formula XIII

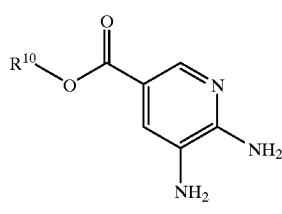

XIII (d) reacting a compound of the Formula XIII wherein $R^{10}$ is an alkyl group with a compound of Formula XIV

XIV

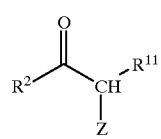

wherein $R^2$ is as defined in claim 1, Z is a leaving group and $R^{11}$ represent H or $CH_3$, in an inert solvent with or without a base to produce a compound of the Formula XV

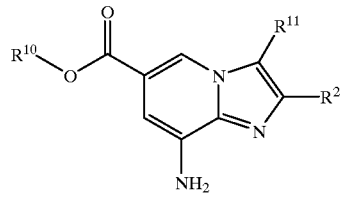

XV (e) reacting a compound of the Formula XV wherein $R^{10}$ is an alkyl group, $R^2$ are as defined in claim 1 and $R^{11}$ is H or $CH_3$ with a compound of Formula IX

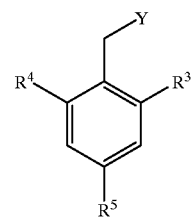

IX wherein $R^3$, $R^4$, and $R^5$ are as defined in claim 1 and Y is a leaving group in an inert solvent with or without a base to produce a compound of the Formula XVI

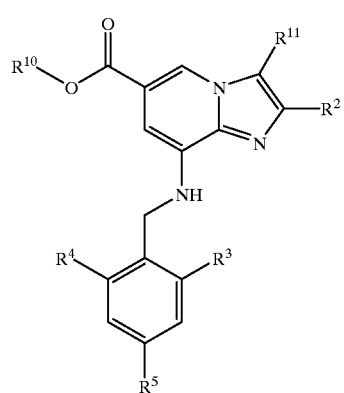

XVI (f) reacting a compound of Formula XVI wherein $R^2$, $R^3$, $R^4$ and $R^5$ are as defined in claim 1, $R^{10}$ is an alkyl group and $R^{11}$ is H or $CH_3$ with a compound of Formula III

III

wherein $R^6$ and $R^7$ are as defined in claim 1, under standard conditions, to produce a compound of Formula I wherein $R^1$ is H or $CH_3$ and X is NH.

10. A process for the preparation of a compound according to any one of claims 1 to 5 comprising (a) treating a compound of Formula XVII

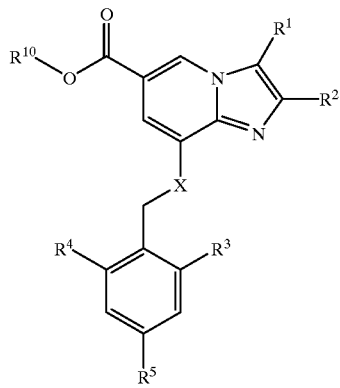

wherein $R^1$, $R^2$, $R^3$, $R^4$, $R^5$ and X are as defined in claim 1 and $R^{10}$ is an alkyl group, with acid or base under standard conditions to produce a compound of Formula XVIII

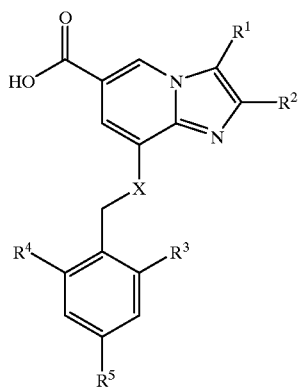

(b) reacting a compound of Formula XVIII wherein $R^1$, $R^2$, $R^3$, $R^4$, $R^5$ and X are as defined in claim 1 with a compound of Formula III

wherein $R^6$ and $R^7$ are as defined in claim 1, in the presence of a coupling reagent in an inert solvent under standard conditions, to produce a compound of Formula I.

11. A pharmaceutical formulation containing a compound or salt thereof according to any one of claims 1 to 5 as active ingredient in combination with a pharmaceutically acceptable diluent or carrier.

12. A method for inhibiting gastric acid secretion which comprises administering to a mammal in need of such inhibition an effective amount of a compound or salt thereof according to any one of claims 1 to 5.

13. A method for the treatment of gastrointestinal inflammatory diseases which comprises administering to a mammal in need of such treatment an effective amount of a compound or salt thereof according to any one of claims 1 to 5.

14. A method for the treatment or prophylaxis of conditions involving infection by *Helicobacter pylori* of human gastric mucosa, which comprises administering to a human in need of such treatment an effective amount of a compound or salt thereof as claimed in any one of claims 1 to 5, wherein the compound or salt thereof is administered in combination with at least one antimicrobial agent.

15. A pharmaceutical formulation for use in the inhibition of gastric acid secretion wherein the active ingredient is a compound or salt thereof according to any one of claims 1 to 5.

16. A pharmaceutical formulation for use in the treatment of gastrointestinal inflammatory diseases wherein the active ingredient is a compound or salt thereof according to any one of claims 1 to 5.

17. A pharmaceutical formulation for use in the treatment or prophylaxis of conditions involving infection by *Helicobacter pylori* of human gastric mucosa, wherein the active ingredient is a compound or salt thereof according to any one of claims 1 to 5 in combination for simultaneous, separate or sequential use together with at least one antimicrobial agent.

18. A compound of the formula VIII

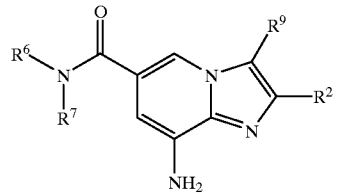

wherein $R^2$ is $CH_3$ or $CH_2CH_3$; $R^6$ and $R^7$ are the same or different and selected from H, $C_1$–$C_6$ alkyl, hydroxylated $C_1$–$C_6$ alkyl or $C_1$–$C_6$ alkoxy-substituted $C_1$–$C_6$ alkyl; and $R^9$ is H, $CH_3$ or an ester group.

19. A compound of the formula X

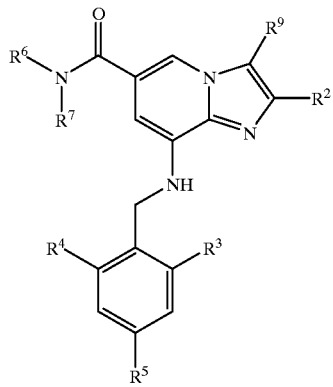

wherein $R^2$ is $CH_3$ or $CH_2CH_3$; $R^3$ is H, $C_1$–$C_6$ alkyl, hydroxylated $C_1$–$C_6$ alkyl or halogen; $R^4$ is H, $C_1$–$C_6$ alkyl, hydroxylated $C_1$–$C_6$ alkyl or halogen; $R^5$ is H or halogen; $R^6$ and $R^7$ are the same or different and selected from H, $C_1$–$C_6$ alkyl, hydroxylated $C_1$–$C_6$ alkyl or $C_1$–$C_6$ alkoxy-substituted $C_1$–$C_6$ alkyl; and $R^9$ is an ester group.

20. A compound of the formula XV

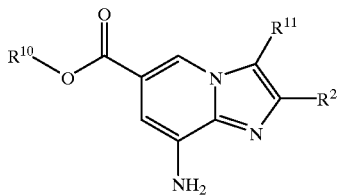

wherein R² is CH₃ or CH₂CH₃; R¹⁰ an alkyl group and R¹¹ is H or CH₃.

21. A compound of the formula XVI

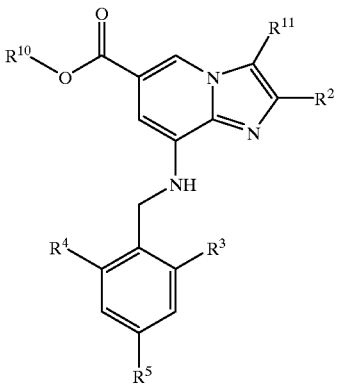

wherein R² is CH₃ or CH₂CH₃; R³ is H, C₁–C₆ alkyl, hydroxylated C₁–C₆ alkyl or halogen; R⁴ is H, C₁–C₆ alkyl, hydroxylated C₁–C₆ alkyl or halogen; R⁵ is H or halogen; R¹⁰ is an alkyl group and R¹¹ is H or CH₃.

22. A compound of the formula

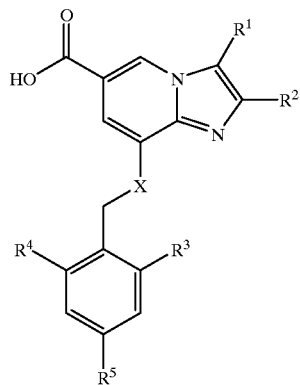

wherein R¹ is H, CH₃ or CH₂OH; R² is CH₃ or CH₂CH₃; R³ is H, C₁₋C₆ alkyl, hydroxylated C₁–C₆ alkyl or halogen; R⁴ is H, C₁–C₆ alkyl, hydroxylated C₁–C₆ alkyl or halogen; R⁵ is H or halogen and X is NH or O.

* * * * *

UNITED STATES PATENT AND TRADEMARK OFFICE
CERTIFICATE OF CORRECTION

PATENT NO.    : 6,313,137 B1                                              Page 1 of 2
DATED         : November 6, 2001
INVENTOR(S)   : Amin et al.

It is certified that error appears in the above-identified patent and that said Letters Patent is hereby corrected as shown below:

Column 8,
Lines 35-51, delete the chemical structures and substitute therefor:

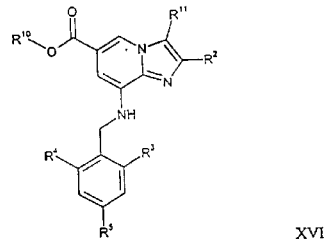

XVI

Column 9,
Lines 38-53, delete the chemical structures and substitute therefor:

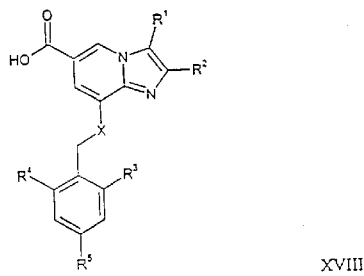

XVIII

UNITED STATES PATENT AND TRADEMARK OFFICE
CERTIFICATE OF CORRECTION

PATENT NO.   : 6,313,137 B1
DATED        : November 6, 2001
INVENTOR(S)  : Amin et al.

It is certified that error appears in the above-identified patent and that said Letters Patent is hereby corrected as shown below:

Column 37,
Line 44, insert -- produce a compound of the -- before "formula XIII".

Column 42,
Line 28, "$C_{1-C6}$" should read -- $C_1$-$C_6$ --.

Signed and Sealed this

Thirteenth Day of August, 2002

*Attest:*

*Attesting Officer*

JAMES E. ROGAN
*Director of the United States Patent and Trademark Office*